US005480774A

United States Patent [19]
Hew et al.

[11] Patent Number: 5,480,774
[45] Date of Patent: Jan. 2, 1996

[54] DETERMINATION OF GENOMIC SEX IN SALMONIDS

[75] Inventors: Choy L. Hew, Thornhill, Canada; Shao J. Du, Seattle, Wash.

[73] Assignee: A/F Protein, Inc., W. Newton, Mass.

[21] Appl. No.: 137,252

[22] Filed: Oct. 14, 1993

[51] Int. Cl.[6] .............................. C12Q 1/68; C12P 19/34; C07H 21/04; C12N 15/00

[52] U.S. Cl. ............................ 435/6; 435/91.1; 435/91.2; 435/270; 435/810; 536/23.1; 536/23.51; 536/24.31; 536/24.33; 935/9; 935/76; 935/77; 935/80

[58] Field of Search ............................... 435/6, 91.1, 91.2, 435/270, 810, 183; 536/23.1, 23.51, 24.31, 24.33; 935/76, 77, 80, 9; 548/303.7; 436/56, 57, 800

[56] References Cited

U.S. PATENT DOCUMENTS 4,683,195  7/1987  Mullis et al. ............................... 435/6

OTHER PUBLICATIONS

Landegren et al., *Science*, vol. 241, pp. 1077–1080, 26 Aug. 1988.
Devlin et al., *Can. J. Fish Aquat. Sci.*, vol. 48, pp. 1606–1612, 1991.
Du et al., I.U.B.S. Toronto Symposium on "Advances in the Molecular Endocrinology of Fish," May 23–25 (1993).
T. Maniatis et al., *Molecular Cloning, a laboratory manual*, published 1982 by McGraw-Hill (N.Y.), pp. 280–281.
Bio/Technology, vol. 3, issued Nov. 1985, Saiki et al., "A novel method for the detection of polymorphic restirction sites by cleavage of oligonucleotide probes: Application to sickle–cell anemia," pp. 1008–1012.
*Nature*, vol. 318, No. 6046, issued 12–18 Dec. 1985, Gill et al., "Forensic application of DNA 'fingerprints'", pp. 577–579.
*Nature*, vol. 335, No. 6189, issued 29 Sep. 1988, Li et al., "Amplification and analysis of DNA sequences in single human sperm and diploid cells," pp. 414–417.

*Primary Examiner*—W. Gary Jones
*Assistant Examiner*—Bradley L. Sisson
*Attorney, Agent, or Firm*—Townsend and Townsend and Crew

[57] ABSTRACT

The invention provides a method for determining the genomic sex of various salmonids (family salmonidae). In particular, the invention provides the nucleic acid sequence of a pseudogene, designated GH-Ψ, which is linked to a sex determining locus on the Y chromosome, and may be used as a marker for determination of the sex of the fish.

26 Claims, 4 Drawing Sheets

DETERMINATION OF GENOMIC SEX IN SALMONIDS

The present invention relates to the isolation of a genetic marker useful for determining the sex of fish belonging to the family salmonidac (salmonids). In particular it relates to the isolation of a growth hormone pseudogene (GH-Ψ), which is linked to a sex-determining locus on the Y chromosome and provides a marker useful for determining the genomic sex of fish.

Because of the depletion of natural stocks of salmon, aquaculture represents an increasingly dominant component of the commercial salmon fishery. For example, aquaculture accounts for the total commercial production of atlantic salmon (*Salmo salar*) on the Atlantic Coast of Canada, while on the Pacific coast, the production of chinook salmon (*Oncorhynchus tshawytscha*) through aquaculture exceeds the combined commercial and recreational catch of wild and hatchery produced chinook salmon.

The rapid growth of chinook salmon aquaculture is closely linked to the development and implementation of sex control biotechnologies for this species (Solar, et al. *Aquaculture '89, World Aqua. Soc., Los Angeles, Calif.* 12–16 Feb. (1989). Female chinook salmon mature at 3, 4, or 5 years of age, while males mature on average one year earlier at 2, 3, or 4 years. The culture of monosex female populations thus provides the aquaculturist with a greater window within which to market this species prior to the development of secondary sexual characteristics. In addition, the use of monoculture female populations avoids the precocious sexual maturation of male fish as grilse which results in significant losses to the farmer due to an unmarketable or low-value product. For these reasons, virtually all of the chinook salmon grown in British Columbia are monosex females.

Monosex populations have been produced by sex-reversing normal (XX) female salmonids by androgen treatment during early development to generate phenotypic males that produce only X-bearing sperm. Hunter, et al., *Aquaculture,* 33:355–364 (1983). This X-bearing sperm is used to fertilize normal ova resulting in all-female offspring for use in production facilities. A small number of XX zygotes can be masculinized to maintain a broodstock of monosex males.

This monosex sperm technology can be combined with triploidy induction to produce monosex female triploid salmonids which are reproductively sterile. It is desirable to maintain sterile salmon because of the increasing concern regarding the potential for genetic interaction between escaped farm fish and wild fish. This is of particular concern where the farmed fish are genetically altered through selection or transgenesis.

The implementation and maintenance of monosex populations requires that genetic and phenotypic sex be independently discernible such that Y-chromosome-bearing males can be distinguished from phenotypic males which carry the female genotype (XX). Traditional methods of sexual determination include identification of morphological differences, or, where there is little sexual dimorphism, examination of gonad tissue. These means however, inherently rely on phenotypic characteristics.

Recently, a marker (designated OtY1) has been identified that indicates the genomic sex of chinook salmon independently of the phenotypic sex (Devlin, et al. *Can. J. Fish. Aquat. Sci.,* 48:1606–1612 (1991). This marker however, appears to be restricted to chinook salmon. Moreover, OtY1 is a repetitive DNA which occurs in several hundred copies. This may tend to confuse results in hybridization and PCR experiments. In addition, since most organisms carry many different types of repetitive DNA in their genome, probes for OtY1 may tend to hybridize with DNA from other species.

The present invention provides a novel marker useful for determining the sex of a number of salmonid species which overcomes these limitations. Moreover, the marker possesses unique features that facilitate the rapid detection of its presence or absence in a particular fish.

SUMMARY OF THE INVENTION

The present invention provides an improved method of determining the genomic sex of a salmonid by detecting the presence or absence of the growth hormone pseudogene GH-Ψ. The pseudogene is detected by amplification of a select subsequence specific to the pseudogene, or by duplex formation of a nucleic acid which hybridizes specifically to the pseudogene and to no other gene in the genome of the salmonid species. The method is useful in a number of salmonids, in particular *Oncorhynchus tshawytscha* and *Oncorhynchus kisutch*.

Where the method involves DNA amplification, such amplification may be accomplished by polymerase chain reaction or ligase chain reaction.

The method may involve identifying the presence or absence of a deletion of about 149 base pairs between exons 5 and 6 in the growth hormone pseudogene of salmonids.

One aspect of the invention relates to pairs of PCR primers for use in detecting the presence or absence of the GH-Ψ. The PCR primers are competent to amplify a DNA sequence which includes a subsequence of exon 5 and intron 5 of the growth hormone gene and pseudogene, wherein one primer of said pair of PCR primers binds selectively to conserved regions of exon 4, intron 4, or exon 5 and the other primer of said pair binds selectively to conserved regions of exon 6, said conserved regions present in both the growth hormone gene and the growth hormone pseudogene.

The invention also provides for a pair of PCR primers competent to amplify the DNA sequence between about base 4870 and base 5019 of Sequence Id No: 1, designated GH-I, wherein one primer of said pair of PCR primers binds selectively to conserved regions of exon 5, and the other primer of said pair binds selectively to conserved regions of intron 5 or exon 6. Preferably the primer pair consists of an oligonucleotide of sequence 5'-CCTGGATGACAATGACTCTCA-3' (SEQ ID No.: 4) and an oligonucleotide of sequence 5'-CTACAGAGTGCAGTTGGCCTC-3' (SEQ ID No.: 5).

Another aspect of the invention relates to probes capable of detecting the presence of the GH-Ψ pseudogene. The probes hybridize specifically to the GH-Ψ pseudogene, but not to the GH-I or GH-II genes in 2x SSC, 0.1% SDS at 42° C. The probes may be selected to hybridize specifically to the region between about base 4843 and base 4863 of Sequence Id No: 2 in 2x SSC, 0.1% SDS at 42° C. The probes may be labeled with a marker such as a fluorophore, a lumiphore, a chromogen, a radioactive label, horseradish peroxidase, biotin, or dioxigenin.

An additional aspect of the invention relates to kits useful for determining the sex of salmonids by detecting the presence or absence of the GH-Ψ pseudogene. These kits take a variety of forms and can comprise one or more containers containing a nucleic acid competent to specifically detect the GH-Ψ pseudogene. The nucleic acid may be a pair of PCR primers, as described above, competent to amplify a DNA subsequence which includes a portion of exon 5 and intron 5 of the GH gene or pseudogene. The nucleic acid may alternatively be a probe, as described above, which hybridizes to the GH-Ψ pseudogene, but not the GH-I or GH-II genes under stringent conditions.

Another aspect of this invention is an isolated nucleic acid which selectively binds to the Sequence Id No.: 2, designated a GH-Ψ pseudogene, said selective binding to occur in genomic libraries of salmon in 0.1x SSC, 0.1% SDS at 42° C. Additionally the invention includes a nucleic acid wherein said nucleic acid is Sequence Id No.: 2.

BRIEF DESCRIPTION OF THE DRAWINGS

FIG. 2 illustrates the detection of the GH-Ψ pseudogene and the GH-II gene in chinook salmon by PCR.

FIG. 3 illustrates the male-specific distribution of GH-Ψ gene in chinook salmon and coho salmon.

Definitions

Figure 1:
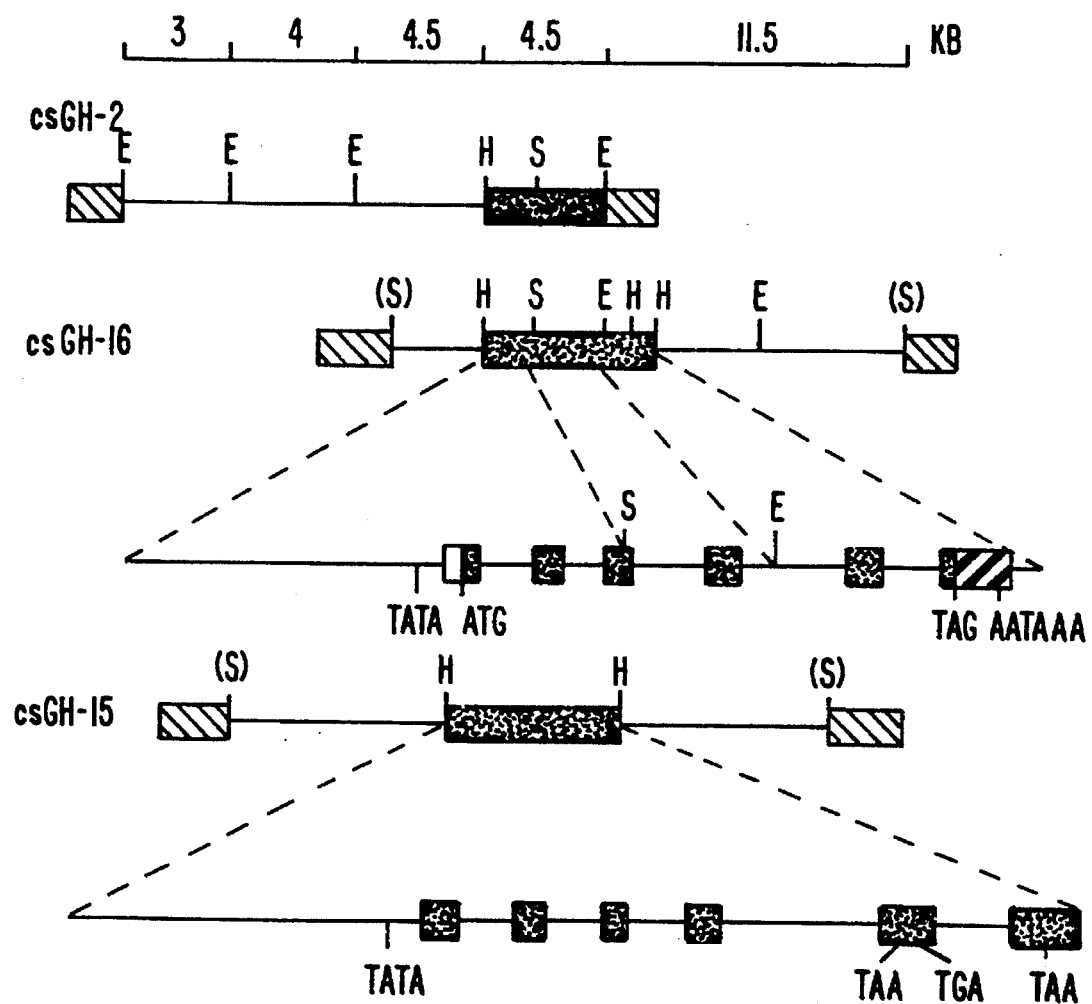
FIG. 1 shows restriction maps of csGH-15, csGH-16 and csGH-2 EMBL clones containing GH genes. Solid boxes in phage DNA denote regions hybridizing to sGH-4. Exons are represented by black boxes. A TATA box, the translation initiation and termination codons, and the polyadenylation signal are indicated by TATA, ATG and TAG/TAA, and AATAAA respectively. Restriction sites are E, EcoR I; H, Hind III; S, Sal I; Sp, Sph I; (S), Sal I site derived from vector arms. It is clear that the restriction map of csGH-15 differs from that of csGH-16. For example, the 6 kb Hind III fragment in csGH-15 covers the entire region which hybridized with the GH-I cDNA; while in csGH-16, there were three Hind III sites in the 6 kb positive region. This indicates that these two clones represented two different GH genes. The restriction map of csGH-2 differed from that of csGH-15 and csGH-16. However, comparing it with the map of csGH16 revealed a 7 kb overlapped region, which suggested that the DNA sequences in these two clones were linked in the chromosome. Thus, a longer map spanning approximately 27.5 kb at the GH locus could be obtained by aligning the map of csGH-2 with that of csGH-16.

The phrase "specifically detect" as used herein refers to the process of determining that a particular subsequence is present in a DNA sample. A DNA sequence may be specifically detected through a number of means known to those of skill in the art. These would include, but are not limited to amplification of the particular target sequence through polymerase chain reaction or ligase chain reaction, hybridization of the sequence to a labeled probe, and binding by labelled ligands or monoclonal antibodies. For a discussion of various means of detection of specific nucleic acid sequences see Perbal, B. *A Practical Guide to Molecular CLoning*, 2nd Ed. John Wiley & Sons, N.Y. (1988) which is incorporated herein by reference.

The phrase "select subsequence" is used herein to refer to a particular DNA subsequence that is of interest. It is often a predetermined or known sequence of nucleic acid bases. A select subsequence is typically chosen because of a unique sequence identity. Typically a select subsequence is one targeted for DNA amplification and often is useful as a specific marker for the presence of a particular gene.

The term "genomic sex" refers to the sex of the fish as indicated by its genotype rather than its phenotype. A male salmonid typically has one X and one Y chromosome (XY), while a female salmonid contains two X chromosomes (XX). Because female salmonids may be masculinized to produce sperm that are genotypically female (XX) phenotypic sexual characteristics may not be diagnostic of genotypic sex.

The term "salmonid" refers to species which are members of the teleost fish family salmonidae. Salmonids include, but are not limited to Atlantic salmon (*Salmo salar*), Chinook Salmon (*Oncorhynchus tschawytscha*), Coho salmon (*Oncorhynchus kisutch*), Chum salmon (*Oncorhynchus keta*), Pink salmon (*Oncorhynchus gorbuscha*), Sockeye salmon (*Oncorhynchus nerka*) , and Rainbow trout (*Oncorhynchus mykiss*).

The term pseudogene is used herein to refer to a growth hormone (GH) gene which cannot be correctly spliced and translated to yield a functional GH. Features of pseudogenes which prevent correct splicing and translation include, but are not limited to, premature stop codons, deletions, and incorrect splicing signals at intron/exon junctions.

The term "subsequence" refers to a sequence of a nucleic acid that comprises a part of a longer sequence of a nucleic acid.

The phrase "conserved region(s)" is used herein to refer to subsequences of the GH genes which differ by less than about 5% of their base composition between the various salmonid GH genes when optimally aligned using conventional sequence analysis computer programs such as CLUSTAL (PC/Gene), GAP or BESTFIT, etc.

The term "oligonucleotide" refers to a molecule comprised of two or more deoxyribonucleotides or ribonucleotides. Oligonucleotides may include, but are not limited to, primers, probes, nucleic acid fragments to be detected, and nucleic acid controls. The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol. 68:90–99; the phosphodiester method of Brown et al., 1979, Meth. Enzymol. 68:109–151; the diethylphosphoramidite method of Beaucage et al., 1981, Tetrahedron Lett. 22:1859–1862; and the solid support method of U.S. Pat. No. 4,458,066.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template.

The phrase "PCR primers competent to amplify" as used herein refers to a pair of PCR primers whose sequences are complementary to DNA subsequences immediately flanking the DNA subsequence (target sequence) which it is desired to amplify. The primers are chosen to specifically bind those particular flanking subsequences and no other sequences present in the sample. The PCR primers are thus chosen to amplify the unique target sequence and no other.

The term "probe" as used herein, refers to a molecule which binds to a specific (select) subsequence of a nucleic acid. A probe is preferably an oligonucleotide which binds through complementary base pairing to a subsequence of a target nucleic acid. It will be understood by one of skill in the art that probes may bind target sequences lacking complete complementarity with the probe sequence depending upon the stringency of the hybridization conditions. The probes are preferably directly labelled as with isotopes, chromophores, lumiphores, chromogens, or indirectly labelled such as with biotin to which a streptavidin complex may later bind. By assaying for the presence or absence of the probe, one can detect the presence or absence of the select subsequence.

The term "nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

The terms "hybridize" or "hybridizing" refer to the binding of two single stranded nucleic acids via complementary base pairing.

The phrase "binding selectively" refers to complementary hybridization between an oligonucleotide and a target sequence and embraces minor mismatches that can be accommodated by reducing the stringency of the hybridization media to achieve the desired priming for the PCR polymerases.

"Amplifying" or "amplification", which typically refer to an "exponential" increase in target nucleic acid, are being used herein to describe both linear and exponential increases in the numbers of a select target sequence of nucleic acid.

The phrase "hybridizing specifically to", refers to the binding of a molecule only to a particular DNA sequence under stringent conditions.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.2 molar at pH 7 and the temperature is at least about 60° C. for long sequences (e.g. greater than about 50 nucleotides) and at least about 42° C. for shorter sequences (e.g. 10 to 50 nucleotides).

The term "SSC" refers to a citrate-saline solution of 0.15M sodium chloride and 20 mM sodium citrate. Solutions are often expressed as multiples or fractions of this concentration. For example, 6x SSC refers to a solution having a sodium chloride and sodium citrate concentration of 6 times this amount or 0.9M sodium chloride and 120 mM sodium citrate. Similarly, 0.2x SSC refers to a solution 0.2 times the SSC concentration or 0.03M sodium chloride and 4 mM sodium citrate.

DETAILED DESCRIPTION

The present invention provides a method for determining the genomic sex of various salmonids (family salmonidae). In particular, the invention provides the nucleic acid sequence of a pseudogene which is linked to a sex determining locus on the Y chromosome, and may be used as a marker for determination of the sex of the fish.

Method of Detecting the GH-Ψ Pseudogene.

The method of the present invention relies on the discovery of a growth hormone gene, designated the GH-Ψ pseudogene which is linked to the sex-determining locus on the Y chromosome of various salmonids. An assay for the presence or absence of this pseudogene, in effect, assays for the presence or absence of the Y chromosome and therefore indicates the genetic sex of the fish.

The assay generally comprises isolating a DNA sample from a particular fish and then contacting that DNA with a nucleic acid competent to specifically detect the GH-Ψ. Two strategies may be utilized for detecting the presence or absence of the GH-Ψ pseudogene. The first strategy involves detection of duplexes formed by a probe which hybridizes specifically to the pseudogene and to no other DNA in the sample. The second strategy involves amplification of GH genes or subsequences and detection of the presence or absence of GH-Ψ by the presence or absence of particular length subsequences among the amplified products.

Isolation of DNA for Detection of GH-Ψ

In a preferred embodiment, DNA will be obtained from species which are members of the family salmonidae. Salmonids include, but are not limited to Atlantic salmon (Salmo salar), Chinook Salmon (Oncorhynchus tschawytscha ), Coho salmon (Oncorhynchus kisutch), Chum salmon (Oncorhynchus keta), Pink salmon (Oncorhynchus gorbuscha), Sockeye salmon (Oncorhynchus nerka), and Rainbow trout (Oncorhynchus mykiss). The method of the present invention is particularly of use in determining the sex of Coho and Chinook salmon. Of course, one of skill would recognize that, given the sequence listings provided herein for GH-I, GH-II and GH-Ψ, it is a relatively straightforward to determine whether the GH-Ψ pseudogene exists in other fish species.

The sexing of a fish using a DNA marker requires that the DNA sequence be accessible to the particular probes used or to the components of the amplification system if the DNA sequence is to be amplified. In general, this accessibility is ensured by isolating the nucleic acids from the sample. DNA may be isolated from a variety of tissues including liver, muscle, blood, and sperm, fins and scales. The choice of tissue is dictated by a number of factors including the quantity of starting material required, the difficulty of isolating DNA from a particular tissue, the possible presence of particular contaminants in a given tissue, and whether or not it is desired that sampling be nonlethal. The choice of tissue is readily apparent to one of skill in the art. In fish, sperm, liver and blood are frequently used as sources of DNA because they provide relatively large amounts of material. In particular, blood provides a tissue which is easily sampled without harm to the organism and, from which DNA is easily extracted.

A variety of techniques for extracting nucleic acids from biological samples are known in the art. For example, see those described by Sambrook et al., *Molecular Cloning—A Laboratory Manual*, Cold Spring Harbor Laboratory, Cold Spring Harbor, N.Y., (1985), by Han, et al. Biochemistry, 26:1617–1625 (1987) and by Du, et al. *Bio/Technology*, 10:176–181 (1992) which are incorporated herein by reference.

Alternatively, if the sample is fairly readily disruptable, the nucleic acid need not be purified prior to amplification by the PCR technique, i.e., if the sample is comprised of cells, particularly peripheral blood lymphocytes or monocytes, lysis and dispersion of the intracellular components may be accomplished merely by suspending the cells in hypotonic buffer or boiling them in a low concentration of alkali (i.e. 10 mM NaOH).

Detection of GH-Ψ Using Hybridization Probes

In one embodiment the GH-Ψ pseudogene may be detected by contacting DNA obtained from the salmonid with a probe which specifically binds the entire GH-Ψ gene or a subsequence of that gene and does not specifically bind to any other DNA sequences in the sample. While such probes may be proteins, oligonucleotide probes are preferred. Typically, the sequence of the oligonucleotide probe is chosen to be complementary to a select subsequence; a subsequence unique to GH-Ψ whose presence or absence is to be detected. Under stringent conditions the probe will hybridize with the select subsequence forming a stable duplex.

The probe is typically labeled and detection of the label in association with the target DNA indicates the presence of the GH-Ψ pseudogene. The probe may be used to detect GH-Ψ directly in a DNA sample without amplification of the GH-Ψ subsequences. For example, unamplified DNA sequences may be probed using a Southern blot. The DNA of the sample is immobilized on a solid substrate, typically a nitrocellulose filter or a nylon membrane. The substrate-bound DNA is then hybridized with the labeled probe under stringent conditions and unhybridized probe is then washed away. Labeled probe detected in association with the immobilized GH sequences (e.g. bound to the substrate) indicates the presence of the GH-Ψ gene. Means for detecting specific DNA sequences are well known to those of skill in the art. Protocols for Southern blots as well as other detection methods are provided in Maniatis, et al. *Molecular Cloning: A Laboratory Manual.* Cold Spring Harbor Laboratory Press, N.Y. (1982) which is incorporated herein by reference.

In another embodiment, the growth hormone gene subsequences are themselves labeled. They are then hybridized, under stringent conditions, with a probe which is immobilized on a solid substrate. Detection of the label in association with the immobilized probe then indicates hybridization of the DNA and the presence of the GH-Ψ pseudogene.

In a preferred embodiment, the GH sequences or subsequences may be amplified by a variety of DNA amplification techniques (for example via polymerase chain reaction, ligase chain reaction, transcription amplification, etc.) prior to detection using a probe. Because the copy number of GH genes is low, the use of unamplified GH DNA results in an assay of low sensitivity. Amplification of GH DNA increases sensitivity of the assay by providing more copies of possible target subsequences. In addition, by using labeled primers in the amplification process, the GH DNA sequences may be labeled as they are amplified.

Selection of Probes for Detection of the GH-Ψ Pseudogene

Full length sequences are provided for the GH-I gene in Sequence Listing No: 1, and for the GH-Ψ gene in sequence listing No: 2. In addition a partial sequence listing for GHII is provided in Sequence listing No: 3. Using these sequence listings, one of skill in the art may easily determine appropriate probes or primers for the detection of the presence or absence of the GH-Ψ pseudogene.

The GH-Ψ pseudogene (Seq. Id. No.: 2) provides a unique marker linked to the sex-determining locus on the Y chromosome. GH-Ψ is closely related to the GH-I and GH-II growth hormone genes in salmon and is most easily described by comparison to the GH-I growth hormone gene.

The GH-I gene consists 6 exons and 5 introns spanning 6.1 kb, including 1.9 kb of 5' flanking sequence, 4.1 kb representing a complete GH transcriptional unit, and 64 bp of 3' flanking sequence. Sequences at the exon-intron junction are consistent with the consensus sequences (GT-AG) at exon-intron boundaries. The size of the 6 exons of GH-I are 74 bp, 140 bp, 117 bp, 156 bp, and 147 bp and 543 bp respectively. A "TATA" box is found in 5' flanking sequence of the GH-I gene 21 bp upstream from the transcriptional initiation site.

The GH-Ψ pseudogene (Seq. Id. No.: 2) resembles the GH-I gene. It has a "TATA" box, and contains six regions corresponding to the six exons in the GH-I gene. However GH-Ψ differs from GH-I in three respects: First, there is an incorrect splicing signal at the intron 1/exon 2 junction, the junction sequence is changed to AC instead of the AG consensus. Second, one premature termination codon is found in exon 5, well before the correct translation stop codon site in exon 6. Third, an approximately 150 bp deletion is identified at the last half of exon 5 and the first part of intron 5; and the occurrence of this deletion event is supported by the identification of two 8 bp direct repeat sequences (GAACCTGG) at the 5' and 3' ends of the deletion. This deletion is comparable to the region in GH-I between base 4870 and base 5019 of Sequence ID No.: 1. In addition, intron 5 of the GH-Ψ pseudogene is about 449 nucleotides shorter than intron 5 of the GH-I gene.

A partial listing of the GH-II gene is provided in Seq. Id No.: 3. GH-II is clearly distinct from the GH-I gene. However, it is almost identical to the corresponding sequence of chum salmon GH-II cDNA (Sekine, et al., *Biochim. Biophys. Acta.* 1009:117–120 (1989), with a characteristic change from Gln135 in GH-I to His135 in GH-II. In addition, there are eight silent mutations within this region compared with GH-I gene, and seven of them match with that in chum salmon GH-II gene. Id. These results confirm that fragment II was indeed amplified from the second GH gene, GH-II, in chinook salmon.

One of skill would recognize that probes that specifically hybridize to the GH-Ψ pseudogene, but not to other GH genes under strict conditions may be readily constructed by exploiting the 150 bp deletion in GH-Ψ or other differences in sequence between the GH-Ψ pseudogene and the GH genes such as the incorrect splicing signal, or the premature stop codon. The design of hybridization probes is well known in the art. See, for example, Sambrook et al., *Molecular Cloning—A Laboratory Manual,* Cold Spring Harbor Laboratory, Cold Spring Harbor, N.Y., (1985) which is incorporated herein by reference.

In a preferred embodiment, the probe is an oligonucleotide sequence complementary to a subsequence spanning the deletion in GH-Ψ, the region around base 4853 in Sequence Listing No.: 2. In addition to complementarity to the subsequence spanning the deletion in GH-Ψ, the probe preferably has destabilizing mismatches with subsequences from other regions of the GH genes. In addition, the probe preferably spans the deletion symmetrically.

The exact length of the probe depends on many factors including the length of conserved regions in GH-I, GH-II, and GH-Ψ, the degree of sequence specificity desired, and the amount of internal complementarity within the probe. Such probes are preferably 17 to 25 bases in length. One of skill would recognize that longer probes would specifically hybridize at higher temperatures. For example, under stringent conditions, e.g. 2x SSC, 0.1% SDS at 42° C., a 25 mer probe complementary to the subsequence spanning the region around base 3505 in Sequence Listing 2 would hybridize to the GH-Ψ pseudogene forming stable duplexes, but would not hybridize to any other nucleic acid sequence in the sample.

Oligonucleotide probes can be prepared by any suitable method, including, for example, cloning and restriction of appropriate sequences and direct chemical synthesis by a method such as the phosphotriester method of Narang et al., *Meth. Enzymol.,* 68:90–99 (1979); the phosphodiester method of Brown et al., *Meth. Enzymol.,* 68:109–151 (1979); the diethylphosphoramidite method of Beaucage et al., *Tetrahedron Lett.,* 22:1859–1862 (1981); and the solid support method of U.S. Pat. No. 4,458,066.

The probe may be labeled by attaching a composition detectable by spectroscopic, photochemical, biochemical, immunochemical, or chemical means. For example, the probe can be labeled at the 5'-end with $^{32}$p by incubating the probe with $^{32}$P-ATP and kinase (see Perbal, *A Practical Guide to Molecular Cloning,* 2nd ed. John Wiley, N.Y. (1988)). Other labels may be joined to the probe directly or through linkers. They may be located at the ends of the probe or internally. Nonradioactive labels for a probe include fluorophores (e.g. fluorescein, rhodamine), lumiphores (e.g luciferase), chromogens (e.g red leuco dye), and horseradish peroxidase (HRP). Methods for labeling and detecting labeled probes are well known in the art and may be found, for example in Connell, et al., *Bio/Techniques* 5:342 (1987) which describes the attachment of fluorophores to oligonucleotides through an amide linkage, and U.S. Pat. Nos. 4,914,210 and 4,962,029 which describe the use of HRP and are incorporated herein by reference. Kits for labelling oligonucleotides are widely available. See, for example, Boehringer Mannheim Biochemicals (Indianapolis, Ind.) for "Genius" labeling kits based on dioxigenin technology and Clonetech (South San Francisco, Calif.) for a variety of direct and indirect oligonucleotide labeling reagents.

Detection of GH-Ψ Through Amplification of Unique Subsequences

The GH-Ψ pseudogene while very similar to the growth hormone genes, contains a 149 bp deletion not present in the GH genes. The existence of this deletion may be exploited to detect the presence or absence of GH-Ψ pseudogene without the use of a hybridization probe. In this approach, subsequences are amplified which span the deletion in GH-Ψ and comparable regions in GH-I and GH-II. The resulting mixture contains amplified subsequences whose lengths reflect the presence or absence of the deletion and thus indicate the presence of the GH-Ψ pseudogene.

Typically three subsequences will be amplified in male fish and two subsequences will be amplified in female fish. Since a GH-I and GH-II gene is present in both males and females, the resulting mixture will include at least two subsequences. The GH-I and GH-II subsequences are distinguishable from each other because the GH-II subsequence between exon 5 and exon 6 is approximately 380 bp shorter than the corresponding GH-I subsequence. In male fish, a third subsequence will be amplified from the GH-Ψ pseudogene. This subsequence is distinguishable from the GH-I and GH-II subsequences because of a shorter intron 5 and by the presence of a 149 bp deletion. Thus, the amplified subsequences may be separated by size allowing determination of the presence or absence of the GH-Ψ pseudogene.

Size separation may be accomplished by a variety of means known to those of skill in the art. These methods include, but are not limited to electrophoresis, density gradient centrifugation, liquid chromatography, and capillary electrophoresis. In a preferred embodiment, the fragments are separated by agarose gel electrophoresis. The bands are then stained with a marker to visualize them such as ethidium bromide and the gel is visualized under ultraviolet light.

As described above, an agarose gel typically shows 3 bands if the fish is male while only two bands if the fish is female (see FIG. 3). If the amplified subsequences completely span intron 5, the bands will differ in length by about 509 bases between the GH-I and GH-Ψ subsequences and by about 380 bases between the GH-I and GH-II subsequences reflecting the differences in size of GH-I and GH-II and the shorter intron 5 and deletion in GH-Ψ.

Selection of Primers for Amplification of GH Marker Sequences

Amplification of GH genes or subsequences may be accomplished by methods well known in the art, which include, but are not limited to polymerase chain reaction (PCR) (Innis, et al., *PCR Protocols. A guide to Methods and Application.* Academic Press, Inc. San Diego, (1990) which is incorporated herein by reference), ligase chain reaction (LCR) (see Wu and Wallace, *Genomics,* 4:560 (1989), Landegren, et al., *Science,* 241:1077 (1988) and Barringer, et al., *Gene,* 89:117 (1990) each of which is incorporated herein by reference), transcription amplification (see Kwoh, et al., *Proc. Natl. Acad. Sci.* (U.S.A.), 86:1173 (1989) which is incorporated herein by reference), and self-sustained sequence replication (see Guatelli, et al., *Proc. Nat. Acad. Sci.* (U.S.A.), 87:1874 (1990) which is incorporated herein by reference), each of which provides sufficient amplification so that the target sequence can be detected by nucleic acid hybridization to a probe or by electrophoretic separation. Alternatively, methods that amplify the hybridization probe to detectable levels can be used, such as Qβ-replicase amplification. See, for example, Kramer, et al. *Nature,* 339:401 (1989), Lizardi, et al. *Bio/Technology,* 6:1197 (1988), and Lomell, et al., *Clin. Chem.* 35:1826 (1989) which are incorporated herein by reference.

In a preferred embodiment, amplification is by polymerase chain reaction using a pair of primers which flank and thereby amplify a selected GH subsequence. Selection of primers is readily apparent to one of skill in the art using the sequence listings of the present invention. For example, the entire GH gene may be amplified using widely spaced primers such as 5'-GAAAATGTTCAATGACT-3' (SEQ ID No.: 6) which is derived from exon 2 of the GH-I gene and 5'-CTCTATCACTCTGAGCT-3' (SEQ ID No.: 7) which is derived from exon 6 of the GH-I gene. Alternatively, the primers may be chosen to amplify only the subsequences which clearly reflect differences between the GH-Ψ pseudogene and other GH genes in the sample. For example, the pair of primers consisting of 5'-CCTGGATGACAATGACTCTCA-3' (SEQ ID No.: 4) which is derived from a conserved sequence in exon 5 and primer G, 5'-CTACAGAGTGCAGTTGGCCTC-3' (SEQ ID No.: 5) which is from a conserved sequence in exon 6 flank and amplify the region spanning a portion of exon 5 and all of intron 5. This region incorporates the deletion in GH-Ψ and therefore reflects the greatest differences between GH-Ψ and GH-I and GH-II.

In order to avoid false negatives due to failure to prime subsequences on one of the GH genes, the primers are chosen to specifically bind regions of the GH genes that are conserved between GH-I, GH-II, and GH-Ψ. Thus subsequences will be amplified from all GH genes present in the sample.

Identification of Conserved GH Sequences

Conserved regions for the purposes of this invention are GH gene subsequences that share at least about 95% sequence identity. "Percentage of sequence identity" is determined by comparing two optimally aligned sequences or subsequences over a comparison window or span, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

A "comparison window" as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Methods of alignment of sequences for comparison are well known in the art. Optimal alignment of sequences for comparison may be conducted by the local homology algorithm of Smith and Waterman, *Adv. Appl. Math.* 2:482 (1981) which is incorporated herein by reference, by the homology alignment algorithm of Needleman and Wunsch *J. Mol. Biol.* 48:443 (1970) which is incorporated herein by reference, by the search for similarity method of Pearson and Lipman, *Proc. Natl. Acad. Sci. (U.S.A.)* 85:2444 (1988) which is incorporated herein by reference, by computerized implementations of these algorithms (including, but not limited to CLUSTAL in the PC/Gene program, Intelligenetics, Mountain View, Calif., GAP, BESTFIT, FASTA, and TFASTA in the Wisconsin Genetics Software Package, Genetics Computer Group (GCG), 575 Science Dr., Madison, Wis.), or by inspection. In particular, methods for aligning sequences using the CLUSTAL program are well described by Higgins and Sharp in Gene, 73:237–244 (1988) and in CABIOS 5:151–153 (1989) both of which are incorporated herein by reference.

Determination of the Presence of the GH-Ψ Marker in Other Salmonid Species

The GH-Ψ pseudogene has been identified in chinook, coho, chum and pink salmon. It further appears to be sex-linked in all of these species. It is therefore reasonable to infer that GH-Ψ may be present in salmonid species not yet screened. One of skill would recognize that the same techniques utilized to identify the presence or absence of GH-Ψ for the purpose of determining the sex of a fish may be utilized to determine if GH-Ψ is present in other species of salmonid. For example, fish species can be screened by extracting DNA from blood, and using primer F (5'-CCTGGATGACAATGACTCTCA-3' (SEQ ID No.: 4)), which is derived from a conserved sequence in exon 5 and primer G, (5'-CTACAGAGTGCAGTTGGCCTC-3' (SEQ ID No.: 5)) which binds a conserved sequence in exon 6 to amplify a subsequences of the GH genes which, when amplified from GH-Ψ incorporate the 150 bp deletion. The amplified subsequences may be separated according to their size as described above. Sequences amplified from fish carrying the GH-Ψ marker will include a pair of subsequences differing in length by about 380 base pairs reflecting the differences length of the subsequences between exon 5 and exon 6 of the GH-I gene and the GH-Ψ pseudogene.

Of course one of skill would recognize other methods of assaying for the presence of GH-Ψ using the primers and probes of the present invention. For example, one might select primer pairs to amplify subsequences containing other regions unique to GH-Ψ pseudogenes. These might include, but are not limited to, the incorrect splicing signal at the intron 1/exon 2 junction or the premature termination codon in exon 5.

Alternatively, one of skill may construct hybridization probes specific to the GH-Ψ pseudogene, but not to the GH-I or GH-II genes. These probes may be specific for the region spanning the 149 base pair deletion in GH-Ψ, or alternatively, they may be specific to other regions of the GH-Ψ pseudogene that are not conserved in the GH-I or GH-II genes. Such regions may be readily identified by one of skill, using the sequence listings provided herein.

In addition to oligonucleotide primers and probes, it is also possible to use growth hormone gene cDNA probes to isolate GH genes in other species. The probes may be specific to GH-Ψ pseudogenes. Alternatively, the probes may hybridize to all homologous GH genes. In the latter case, the genes, once isolated, may be sequenced. Analysis of the sequence data will reveal the presence or absence of GH-Ψ pseudogenes. Techniques for the use of cDNA probes to isolate genes and subsequent sequencing are well known in the art (See Maniatis, et al. Molecular Cloning: A Laboratory Manual. Cold Spring Harbor Laboratory Press, NY (1982)).

Determining if the GH-Ψ Pseudogene is Sex-Linked

Once it is determined that the GH-Ψ pseudogene is present in a particular fish species, it is necessary to verify that GH-Ψ is linked to a sex-determining locus on the Y chromosome. To accomplish this a number of both males and females of the species are screened by the one of procedures described above for detecting the presence or absence of a GH-Ψ pseudogene. The sex of the fish must then be verified using another approach such as examination of gonads. If the GH-Ψ pseudogene is sex-linked, it should co-segregate with the males.

To verify that the apparent association of the GH-Ψ pseudogene with males is not simply due to the occurrence or non-occurrence of a particular polymorphism rather than actual sex-linkage, the distribution of the GH-Ψ pseudogene must be examined within a family of fish. If the males bear the GH-Ψ pseudogene, but the females do not, it will indicate both that the marker is present in the fish and that it segregates as a sex-linked marker.

Kits for Determining the sex of Salmonids

The present invention also relates to kits, multicontainer units comprising useful components for practicing the present method. A useful kit can comprise a container containing a pair of primers competent to specifically detect the GH-Ψ pseudogene and/or a probe specific to the GH-Ψ pseudogene. In some cases, the probe may be fixed to an appropriate support membrane. The probe or the primers may be labeled.

Other optional components of the kit include, for example, a polymerase, the substrate nucleoside triphosphates, means used to label (for example, an avidin-enzyme conjugate and enzyme substrate and chromogen if the label is biotin), the appropriate buffers for PCR or hybridization reactions, and pre-cast gels for electrophoresis. In addition to the above components, the kit can also contain instructions for carrying out the present method.

The following examples are offered to illustrate, but not to limit the present invention.

EXAMPLE 1

Detection of the Presence Absence of GH-Ψ

To test for the presence of GH-Ψ genes, chinook salmon genomic DNA was analyzed by PCR. To isolate DNA from sperm, 2 μl of sperm was suspended in 100 μl of 1 x PCR buffer (50 mMKCl, 10 mM Tris-HCl pH 8.8, 1.5 mMMgCl$_2$, 0.1% p-octylphenoxypolyethoxyethanol type TRITON® X-100), followed by the addition of 3 μl of proteinase K (10 mg/ml). The sample was incubated for 2 hours at 55° C., and then mixed with 100 μl of 10 mM NaOH. The mixture was boiled for 3 min and centrifuged for 3 min.

About 100 ng of DNA (3 μl of the supernatant) was amplified by PCR using two GH specific primers designated F and G. Primer F, 5'-CCTGGATGACAATGACTCTCA-3' (SEQ ID No.: 4), was derived from a conserved sequence in exon 5 in both GH-I and GH-Ψ, while primer G, 5'-CTACAGAGTGCAGTTGGCCTC-3' (SEQ ID No.: 5), was from a conserved sequence in exon 6 in both genes. A positive control was provided using, 40 ng each of plasmid DNA for the GH-I gene and the GH-Ψ gene. The PCR reaction and the analysis of the PCR products were carried out essentially as described by Du, et al. Bio/Technology, 10:176–181 (1992), which is incorporated herein by reference. PCR cycling parameters were 1 min at 94° C. 1 min at 60° C., and 2 min at 72° C.

Figure 2A:
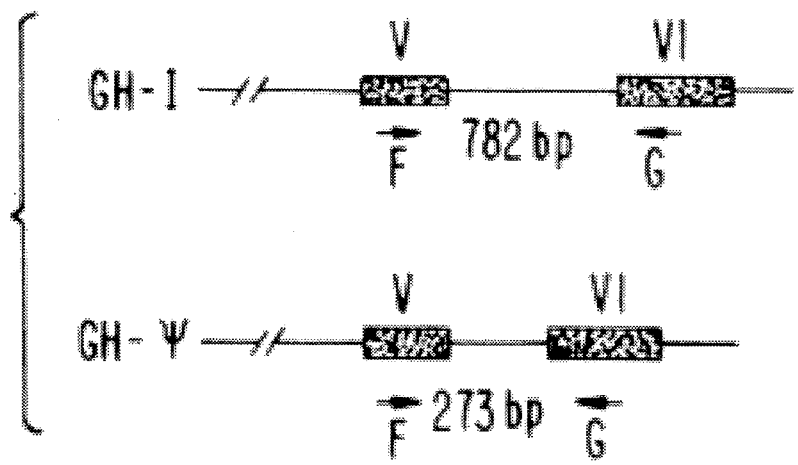
FIG. 2(A) illustrates the PCR strategy. Primers F and G are derived from part of the conserved sequences in exon V and VI of GH-I and GH-Ψ genes respectively. The distance between primers F and G in GH-I and GH-Ψ genes is 782 bp and 271 bp respectively.

Primers F and G, shown in FIG. 2(A), were derived from the sequences in exon 5 and 6 respectively, separated by intron 5. These primers were chosen to take advantage of the observation that the size of this intron differs between GH-I gene and GH-Ψ. Thus, PCR using primers F and G, should generate two fragments of 782 bp and 273 bp from GH-I and GH-Ψ respectively (FIG. 2(A)).

Figure 2B:
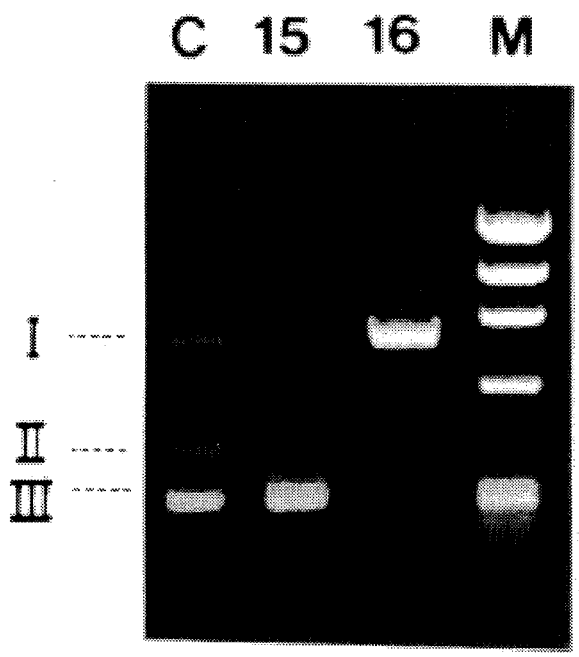
FIG. 2(B) shows the analysis of the PCR products by agarose gel electrophoresis. The gel was stained with ethidium bromide. The three PCR fragments are designated as I, II and III. Lane C represents chinook salmon genomic DNA from a male fish; Lane 16 represents a plasmid clone of GH-I gene; Lane 15 represents a plasmid clone of GH-Ψ pseudogene; Lane M represents molecular weight markers (fx-174-RF DNA Hae III digest).

However, PCR analysis showed that, in addition to the 782 bp (fragment I) and the 273 bp (fragment III) bands, a third band approximately at 400 bp (fragment II) was amplified (FIG. 2 (B)).

In order to clarify the nature of fragment II, and to confirm that fragments I and III were indeed amplified from GH-I and GH-Ψ respectively, the three PCR fragments were gel purified, treated with T4 DNA polymerase to create blunt ends, cloned into pUC18 Sma I site by blunt end ligation, and sequenced.

The sequence data show that fragment I was indeed derived from the GH-I gene. Similarly, the sequence of fragment III was identical to the corresponding region of GH-Ψ (data not shown). The sequence of fragment II is shown in Sequence Id No.: 3. Comparison with the sequences of chinook salmon GH-I (Ot), chum salmon (Ok) GH-I and GH-II, clearly shows that it is distinct from that of GH-I. This suggests that it represents a different GH gene. However, it is almost identical to the corresponding sequence of chum salmon GH-II cDNA, as described by Sekine, et al., Biochem. Biophys. Acta., 1009:117–120 (1989), with a characteristic change from Gln135 in GH-I to His135 in GH-II. This change is also true for GH-II in rainbow trout. See Agellon, et al., Proc. Natl. Acad. Sci. (U.S.A.), 85:5136–5140 (1988) and Rentier-Delrue, et al., DNA, 8:109–117 (1989). In addition, there are eight silent mutations within this region compared with GH-I gene, and seven of them match with that in chum salmon GH-II gene described by Sekine, et al., Biochim. Biophys. Acta., 1009:117–120 (1989). All these results confirm that fragment II was indeed amplified from a second GH gene, GH-II, in chinook salmon.

EXAMPLE 2

Distribution and Sex-Linkage of GH-Ψ DNA

To examine the distribution of the three GH genes in chinook salmon, 50 unrelated chinook salmon (25 males and 25 females) were analyzed by PCR using the GH specific primers F (5'-CCTGGATGACAATGACTCTCA-3' (SEQ ID No.: 4)) and G (5'-CTACAGAGTGCAGTTGGCCTC-3' (SEQ ID No.: 5)) described in Example 1 and shown in FIG. 2(A). DNA was isolated from blood cells from individual fish. The DNA isolation and PCR amplification were carried out essentially as described by Du, et al. Bio/Technology, 10:176–181 (1992).

Figure 3A:
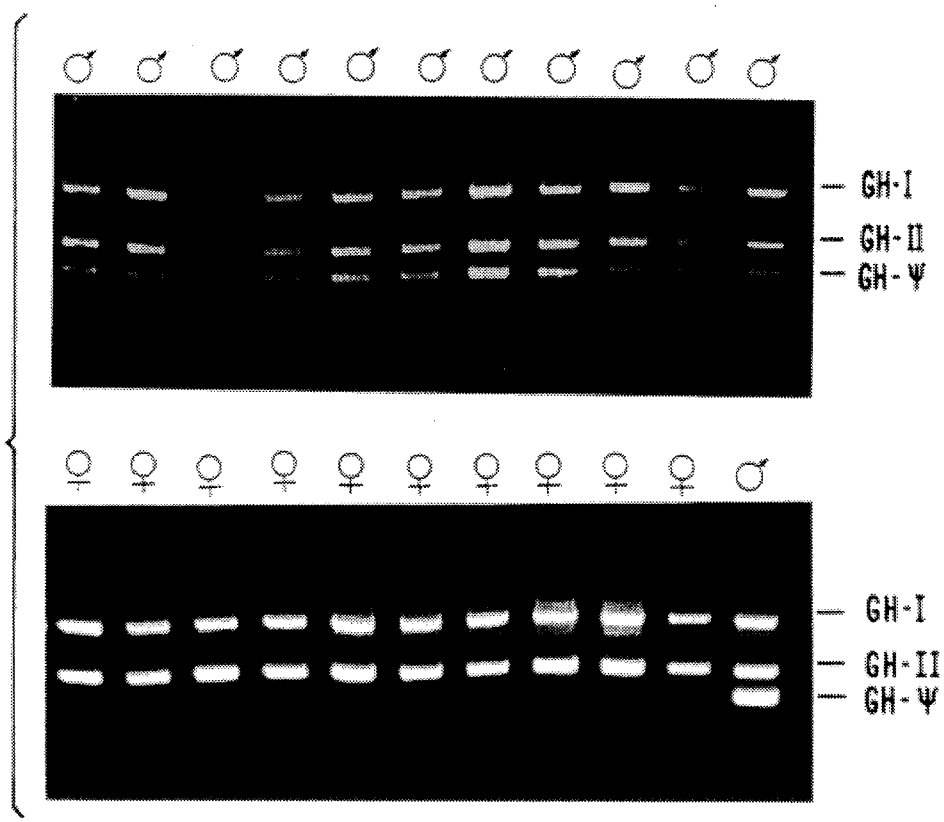
FIG. 3(A) shows the results of a PCR analysis, using primers F and G, of 50 chinook salmon (25 males and 25 females). GH-Ψ is found present only in the males. Data from 11 males and 10 females are shown here.
Figure 3B:
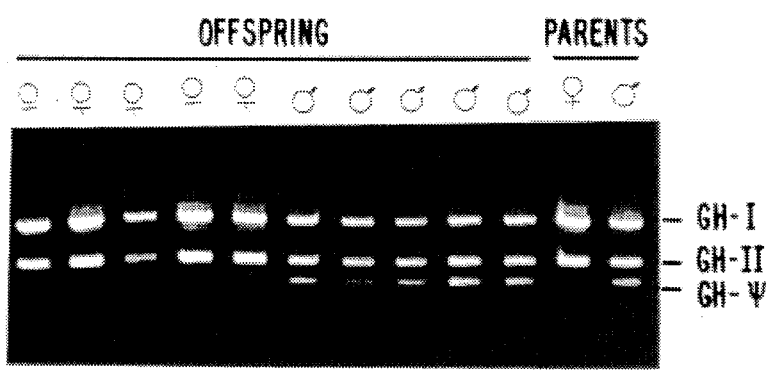
FIG. 3(B) shows a chinook salmon family analysis of the distribution of GH-Ψ by F/G PCR. One chinook salmon family containing both parents and five each of male and female offspring were used. Three GH genes (GH-I, GH-II and GH-Ψ) were found in males, two GH genes (GH-I and GH-II) in females.
Figure 3C:
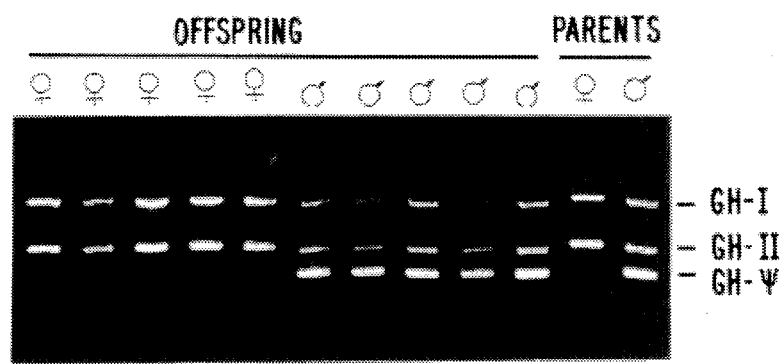
FIG. 3(C) shows a family analysis of the distribution of the GH-Ψ in coho salmon (Oncorhynhus kisutch) by PCR using the same set of primers.

The PCR data showed sex-linked distribution patterns (FIG. 3). Three DNA fragments corresponding to GH-I, GH-II and GH-Ψ were amplified from males, however, only two of these fragments corresponding to GH-I and GH-II were generated in females (FIG. 3(A)). This suggested that GH-Ψ may be male specific.

To confirm this observation, a chinook salmon family containing both parents and five each of male and female offspring were analyzed by PCR using the same set of primers. It was found that the male parent and their male offspring had the extra GH-Ψ gene, while the female parent and the female offspring lacked GH-Ψ (FIG. 3(B)), further demonstrating that GH-Ψ is male specific.

To test whether the GH pseudogene exists in other salmonids, the genomic DNA of males and females from pink, coho, sockeye, chum, and Atlantic salmon, and from rainbow trout were analyzed by PCR using primers F and G. The results showed that the coho salmon is similar to chinook salmon in that the male has three bands while the female has two bands. Family studies in coho salmon confirmed that the pseudogene is male specific (FIG. 3(C)).

EXAMPLE 3

Number of GH Genes in Chinook Salmon

To verify that there are only three GH genes in chinook salmon, a genomic Southern analysis was performed. Chinook salmon genomic sperm DNA (20 μg) was digested with restriction enzyme EcoR V, Sst I and Sca I separately. The digested DNA was separated by 0.7% agarose gel in 1x TNE buffer at 65 mA for 6 hours. The DNA was transferred to Hybond-N nylon membrane (Amersham) using 10x SSC buffer for 24 hours. The filter was prehybridized with buffer containing 10% dextran sulfate, 1M NaCl, 1% SDS, 50% formamide and 200 mg/ml of sheared calf thymus DNA for 20 min at 42° C. and followed by hybridizing with 32p labeled complete chinook salmon GH cDNA in the same buffer system. The hybridization was carried out for 18 hours at 42° C. After hybridization, the filters were washed once with 2xSSC (0.3M NaCl, 0.034M sodium citrate) for 15 min at room temperature, twice with 2xSSC, 0.1% SDS for 15 min at 65° C., and once with 0.1xSSC, 0.1% SDS for 10 min at 65° C. The filters were air dried at room temperature and exposed to X-ray film for 2 days at −70° C.

Figure 4:
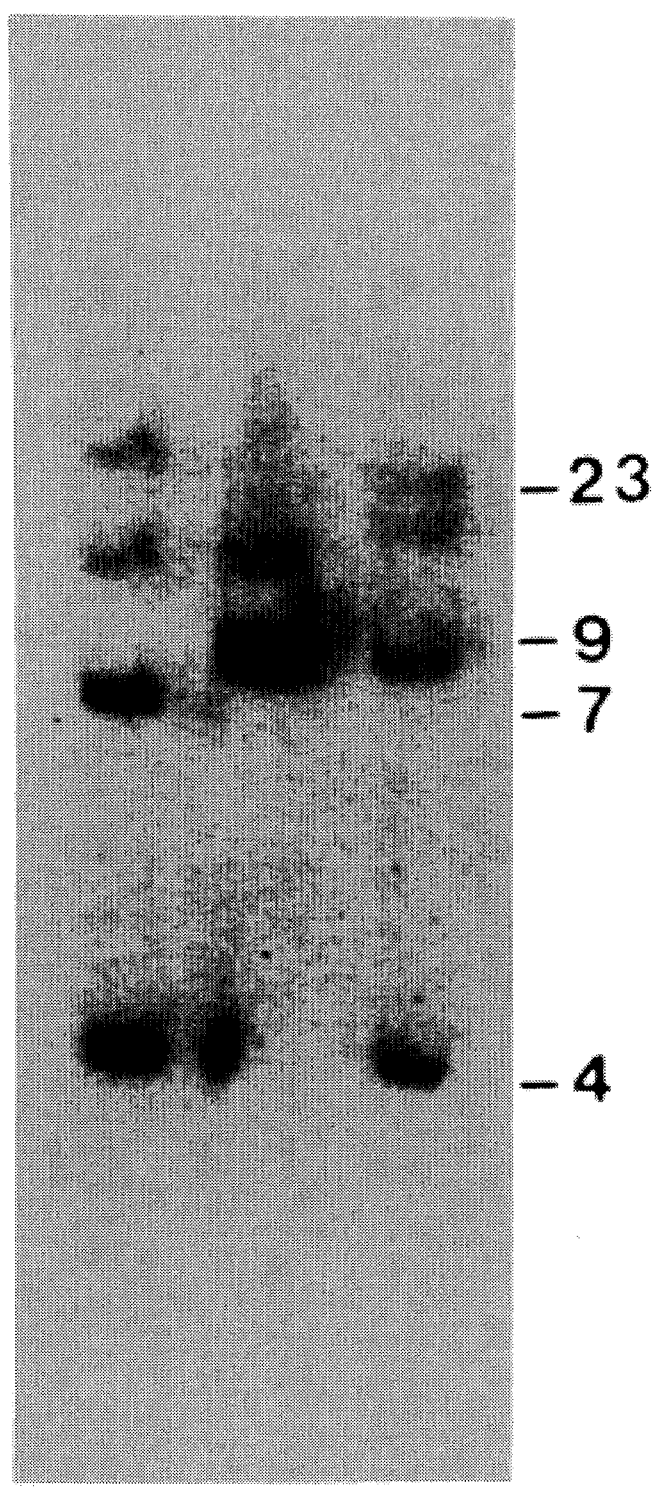
FIG. 4 shows the results of a genomic Southern blot to determine the number of GH genes present in chinook salmon. Genomic DNA from male chinook salmon was digested with EcoR I (EV), Sst I (Ss) and Sca I (Sc), and probed with chinook salmon GH-I cDNA. The size of the positive bands was estimated by comparing to the molecular weight marker (λDNA-Hind III digest).

As shown in FIG. 4, four positive bands approximately at 5 kb, 7.5 kb, 18 kb and 27 kb were generated by digestion with EcoR V. Digestion with Sca I also gave four positive bands at approximately 5 kb, 8 kb, 20 kb, and 25 kb. The DNA sequence data shows that there is neither an Eco RV nor a Sca I recognition site in GH-I gene, so that only one fragment could be generated from GH-I gene by these two enzymes. However, there is one Eco RV and one Sca I recognition site in GH-Ψ. The Eco RV site is located in exon III, while the Sca I site is located in exon IV. Since both of these sites are located in the middle of the gene, two positive fragments therefore could be generated from the pseudogene alone by a single digestion with either one of these two restriction enzymes. As a result, total of three fragments should be generated from GH-I and GH-Ψ. However, Southern analysis revealed four positive bands in both digestions, and the largest fragments by Eco RV or Sca I digestion were 27 kb and 25 kb respectively. It is unlikely that either of these two 27 kb and 25 kb fragments contains more than one GH gene since restriction mapping showed that the GH-I gene locus spans at least 27.5 kb (FIG. 1). Therefore, the extra positive band must come from a third GH gene, the GH-II gene. Overall, these results strongly suggest that there are only three GH genes in the male chinook salmon genome, i.e., GH-I, GH-II and a pseudogene, GH-Ψ.

EXAMPLE 4

Determination of the Sex of Oncorhynchus tshawytscha

DNA is isolated from the blood cells of an individual fish essentially as described by Du, et al. *Bio/Technology*, 10:176–181 (1992) PCR amplification is carried out using oligonucleotide primers F and G which are 5'-CCTGGAT-GACAATGACTCTCA-3' (SEQ ID No.: 4) and 5'-CTACA-GAGTGCAGTTGGCCTC-3' (SEQ ID No.: 5) respectively. The PCR reaction and the analysis of the PCR products is carried out essentially as described by Du, et al. (1992). PCR cycling parameters are 1 min at 94° C., 1 min at 60° C., and 2 min at 72° C.

The amplified PCR products are analyzed by agarose gel electrophoresis. The gel is stained with ethidium bromide to visualize the separated gene fragments.

The distance between primers F and G in GH-I and GH-Ψ and GH-II genes is 782 bp, 273 bp and about 400 bp respectively. Thus, amplified products from male fish produce three bands on an agarose gel, corresponding to subsequences from GH-I, GH-Ψ, and GH-II, while amplified products from female fish produce 2 bands corresponding to subsequences from GH-I and GH-II.

What is claimed is:

1. A method of determining genomic sex of a member of the genus Oncorhynchus of the salmonid family by detecting a presence or absence of a growth hormone pseudogene (GH-Ψ), said method comprising:

obtaining DNA from a salmonid species in which only males carry the GH-Ψ pseudogene; and detecting the GH-Ψ, where said detecting includes either the amplification of a select subsequence specific to the pseudogene or duplex formation of a nucleic acid hybridizing specifically to the pseudogene and to no other genome of the salmonid species.

2. The method of claim 1 wherein said amplification is by polymerase chain reaction.

3. The method of claim 2 wherein said polymerase chain reaction utilizes a pair of PCR primers competent to amplify a DNA sequence which includes a subsequence of exon 5 and intron 5 of the growth hormone gene and pseudogene, wherein one primer of said pair of PCR primers binds selectively to conserved regions of exon 4, intron 4, or exon 5 and the other primer of said pair binds selectively to conserved regions of exon 6, said conserved regions present in both the growth hormone gene and the growth hormone pseudogene.

4. The method of claim 2 wherein said polymerase chain reaction utilizes a pair of PCR primers competent to amplify the DNA sequence between about base 4870 and base 5019 of Sequence Id No: 1, designated GH-I, wherein one primer of said pair of PCR primers binds selectively to conserved regions of exon 5, and the other primer of said pair binds selectively to conserved regions of intron 5 or exon 6.

5. The method of claim 4 where said pair of PCR primers consists of an oligonucleotide of sequence 5'-CCTGGATGACAATGACTCTCA-3' (SEQ ID No.: 4) and an oligonucleotide of sequence 5'-CTACAGAGTGCAGTTGGC-CTC- 3' (SEQ ID No.: 5).

6. The method of claim 1 wherein said amplification is by ligase chain reaction.

7. The method of claim 1 wherein said presence or absence of a growth hormone pseudogene is the detection of a deletion of about 149 base pairs between exons 5 and 6 in the growth hormone genes of salmonids.

8. The method of claim 1 wherein said nucleic acid is a nucleic acid probe which hybridizes specifically to Sequence Id No.: 2, but not Sequence Id No.: 1 or Sequence Id No.: 3 in 2x SSC, 0.1% SDS at 42° C.

9. The method of claim 8 wherein said probe hybridizes specifically to the region between about base 4843 and base 4863 of Sequence Id No: 2 in 2x SSC, 0.1% SDS at 42 C.

10. The method of claim 9 wherein said probe is labeled with a marker selected from the group consisting of: a fluorophore, a lumiphore, a chromogen, a radioactive label, horseradish peroxidase, biotin, or dioxigenin.

11. The method of claim 1 wherein said salmonid species is selected from the group consisting of Oncorhynchus tshawytscha, and Oncorhynchus kisutch.

12. A composition comprising a pair of PCR primers competent to amplify a DNA sequence which includes a subsequence of exon 5 and intron 5 of a growth hormone gene and a pseudogene from a salmonid, wherein one primer of said pair of PCR primers binds selectively to conserved regions of exon 4, intron 4, or exon 5 and the other primer of said pair binds selectively to conserved regions of exon 6, said conserved regions present in both the growth hormone gene and the growth hormone pseudogene.

13. The composition of claim 12 wherein said pair of PCR primers are competent to amplify a DNA subsequence between about base 4870 and base 5019 of Sequence Id No.: 1, designated GH-I, which includes a subsequence of exon 5 and intron 5 of the GH gene or pseudogene, said primers binding selectively to exon 5 and exon 6.

14. The composition of claim 13 where said pair of PCR primers consists of an oligonucleotide of sequence 5'-CCTGGATGACAATGACTCTCA-3' (SEQ ID No.: 4) and an oligonucleotide of sequence 5'-CTACAGAGTG-CAGTTGGCCTC-3' (SEQ ID No.: 5).

15. A composition of claim 12 wherein the member of the genus Oncorhynchus is selected from the group consisting of O. tshawytscha and O. kisutch.

16. A nucleic acid probe which specifically detects a GH-Ψ pseudogene wherein said probe is a nucleic acid which hybridizes specifically to Sequence Id No.: 2, but not Sequence Id No.: 1 or Sequence Id No.: 3 in 2x SSC, 0.1% SDS at 42° C.

17. The probe of claim 16 wherein said probe hybridizes to the region between about base 4843 and base 4863 of Sequence Id No: 2 in 2x SSC, 0.1% SDS at 42° C.

18. The probe of claim 17 wherein said probe is labeled with a marker selected from the group consisting of: a fluorophore, a lumiphore, a radioactive label, horseradish peroxidase, biotin, or dioxigenin.

19. A kit useful for determining the genomic sex of a member of the genus Oncorhynchus of the salmonid family by detecting the presence or absence of a growth hormone pseudogene which comprises a container containing an isolated oligonucleotide for the amplification of a unique subsequence of the growth hormone pseudogene or hybridizes specifically to the growth hormone pseudogene.

20. The kit of claim 19 wherein said nucleic acid is a pair of PCR primers competent to amplify a DNA subsequence which includes a portion of exon 5 and intron 5 of the GH gene or pseudogene from a salmonid, wherein one primer of said pair of PCR primers binds selectively to conserved regions of exon 4, intron 4, or exon 5 and the other primer of said pair binds selectively to conserved regions of exon 6.

21. The kit of claim 20 wherein said nucleic acid is a pair of PCR primers able to amplify a DNA sequence between about base 4870 and base 5019 of Sequence Id No.: 1, which includes a portion of exon 5 and intron 5 of the GH gene or pseudogene, wherein one primer of said pair of PCR primers binds selectively to conserved regions of exon 5 and the other primer of said pair binds selectively to conserved regions of intron 5 or exon 6.

22. The kit of claim 21 where said pair of PCR primers consists of an oligonucleotide of sequence 5'-CCTGGATGACAATGACTCTCA-3' (SEQ ID No.: 4) and an oligonucleotide of sequence 5'-CTACAGAGTGCAGTTGGC-CTC-3' (SEQ ID No.: 5).

23. The kit of claim 19 wherein said nucleic acid is a nucleic acid probe which hybridizes specifically to Sequence Id No.: 2, but not Sequence Id No.: 1 or Sequence Id No.: 3 in 2x SSC, 0.1% SDS at 42° C.

24. The kit of claim 23 wherein said probe hybridizes specifically to a region between about base 4843 and base 4863 of Sequence Id No: 2 in 2x SSC, 0.1% SDS at 42° C.

25. The kit of claim 24 wherein said probe is labeled with a marker said marker is selected from the group consisting of: a fluorophore, a lumiphore, a radioactive label, a chromogen, horseradish peroxidase, biotin, or dioxigenin.

26. The kit of claim 19 wherein said salmonid is selected from the group consisting of *Oncorhynchus tshawytscha*, and *Oncorhynchus kisutch*.

\* \* \* \* \*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 6136 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinook Salmon ( i x ) FEATURE:
        ( A ) NAME/KEY: exon
        ( B ) LOCATION: 1904..1980

( i x ) FEATURE:
        ( A ) NAME/KEY: intron
        ( B ) LOCATION: 1981..2383

( i x ) FEATURE:
        ( A ) NAME/KEY: exon
        ( B ) LOCATION: 2384..2523

( i x ) FEATURE:
        ( A ) NAME/KEY: intron
        ( B ) LOCATION: 2524..2659

( i x ) FEATURE:
        ( A ) NAME/KEY: exon
        ( B ) LOCATION: 2660..2776

( i x ) FEATURE:
        ( A ) NAME/KEY: intron ( B ) LOCATION: 2777..3498

( i x ) FEATURE:
            ( A ) NAME/KEY: exon
            ( B ) LOCATION: 3499..3654

( i x ) FEATURE:
            ( A ) NAME/KEY: intron
            ( B ) LOCATION: 3655..4786

( i x ) FEATURE:
            ( A ) NAME/KEY: exon
            ( B ) LOCATION: 4787..4933

( i x ) FEATURE:
            ( A ) NAME/KEY: intron
            ( B ) LOCATION: 4934..5529

( i x ) FEATURE:
            ( A ) NAME/KEY: exon
            ( B ) LOCATION: 5530..5592

( i x ) FEATURE:
            ( A ) NAME/KEY: CDS
            ( B ) LOCATION: join(1971..1980, 2384..2523, 2660..2776, 3499
                ..3654, 4787..4933, 5530..5592)

( i x ) FEATURE:
            ( A ) NAME/KEY: mat_peptide
            ( B ) LOCATION: join(2440..2523, 2660..2776, 3499..3654, 4787
                ..4933, 5530..5592)

( i x ) FEATURE:
            ( A ) NAME/KEY: sig_peptide
            ( B ) LOCATION: join(1971..1980, 2384..2439)

( i x ) FEATURE:
            ( A ) NAME/KEY: misc_feature
            ( B ) LOCATION: 1..6136
            ( D ) OTHER INFORMATION: /standard_name="The Complete
                Nucleotide Sequence of Chinook Salmon GH-I Gene"

( i x ) FEATURE:
            ( A ) NAME/KEY: misc_feature
            ( B ) LOCATION: 577..843
            ( D ) OTHER INFORMATION: /note="The 266 bp 5'flanking
                homologous region shared with the GH pseudo..."

( i x ) FEATURE:
            ( A ) NAME/KEY: misc_feature
            ( B ) LOCATION: 1805..1808
            ( D ) OTHER INFORMATION: /standard_name="The CAAT Box"

( i x ) FEATURE:
            ( A ) NAME/KEY: misc_feature
            ( B ) LOCATION: 1878..1885
            ( D ) OTHER INFORMATION: /standard_name="The TATA Box"

( i x ) FEATURE:
            ( A ) NAME/KEY: misc_feature
            ( B ) LOCATION: 6051..6056
            ( D ) OTHER INFORMATION: /standard_name="The
                Polyadenylation Signal"

( x i ) SEQUENCE DESCRIPTION: SEQ ID NO:1:

| | | | | | |
|---|---|---|---|---|---|
| CCCCAAAACC | AATTCTTTCT | TTGGCCGCCT | CTCCTTCCAG | TTCTCTGCTG | CCAATGACTG | 60 |
| GAACGAACTA | CAAAAATCTC | TGAAACTGGA | AACACTTATC | TCCCTCACTA | GCTTTAAGCA | 120 |
| CCAACTGCCA | GAGCAGCTCA | CAGATTACTG | CACCTGTACA | TAGCCCACCT | ATAATTTAGA | 180 |
| CCAAACAACT | ACCTCTTTCC | CTACTGTATT | TAATTGATTT | ATTTATTTTG | CTCCTTTGCA | 240 |
| CCCCATTATT | TTTATTTCTA | CTTTGCACAT | TCTTCCATTG | CAAATCTACC | ATTCCAGTGT | 300 |
| TTTACTTGCT | ATATTGTATT | TACTTTGCCA | CCATGGCCTT | TTTTGCCTT | TACCTCCCTT | 360 |
| ACTCTACCTC | ATTTGCTCAC | ATCGCATATA | GACTTGTTTA | TACTGTATTA | TTGACTGTAT | 420 |

-continued

```
GTTTGTTTTA CTCCATGTGT AACTCTGTGT CGTTGTATGT GTCGAACTGC TTTGCTTTAT      480
CTTGGCCAGG TCGCAATTGT AAATGAGAAC TTGTTCTCAA CTTGCCTACC TGGTTAAATA      540
AAGGTGAAAT ATTTTTTTT AAATAAAATA AAATACAGTA TTTTTGATTT GCTGTACTCT       600
CAAAACAAGT CATCCCTACA TCCAATCTGA TAGTGTGGCC GAAACTAACC GTTGTATAGT      660
GCTCTTTTGA AAGCCAAGCT ACCACATATT CAACGAGGTA ATGAGGTCAG TAAATGCACT      720
TTCGGCCGCC CTTCCAAAGT GATGTGGGTT AACAGATCGA TTTCTGTTTT TGCCAGGAAA      780
GGATTAGGAC AGCGCTGGGC CTGACATTCA GCACGTCTCC GTGTCCTGAA CACTGAATAT      840
GGATCTAGGT TGAATATGTT CACCCAACTT AGGTTGAACA TGTTCACACC GGAACAGTCT      900
ACTCCCCCGT ATGCCACGCT GACATGATCT CATTACTGTC ATGACTATTG ACCAGATAAC      960
CTTTATAGGT GCCATGACAC CTTACACCTA CATGTGTATC GTAAACAATA CAGTAAGGTG     1020
GTGCGGCACA AACAGAGTGT AGGCTTTGGG CTGGTAACAT TGTGTAGTCA AGCACACATG     1080
CTGCTAGGCT GAAAGCAGTT CATGTGTTAT CCTCTGAGAT GTATACTTTT TTAACAGCA      1140
TATACATTTT TCCCCCAAAA TCAATCAATC AATCAACGGA TGAAGTAGGG CCTGCACACT     1200
TGCTCCAATA GATACCGTTA TTAGGCTTTC TTGACAATGT TGAGATTACT GAAAGGATCT     1260
TCGTCAGGTA TGACAAAGGC TCTCACACAA AAGAAAAAG GATCGGGTAT TTCACAGACT      1320
GGTATTGATC AAGTGACTCT TTATGTTGTG TGTGTTGATG ATAACAAAGA CCCTGTCTGA     1380
ATTTAAACAA AAAACTATAC ATTCTAACAT GTGCCGTCTC GAGTCCTTCT CTGTGTGTCT     1440
ACTTTGAGGA ATTTGACTAA GTGTTAATGC CATAGGACAT TCAATTTGAC ATTAAACAAT     1500
AACATATTGG GGTTAATAAA GAAGCAATAT AATAAATGTC TTGTCATACT GCCTGTTATC     1560
TACAGTACCA CAGCAGAATG GCAGAATAAC CTGTGTGTGT GTGTGTGTGT GTATCTTATG     1620
TCCATTCATT ACATCCTAGA CAACAGAGGT TTGTGTTGTA TGTGTTTTGA CCCTAATTCG     1680
TTCAGTCATC AAGTAAGTTG TTTTTTTAGG ACACCTCCCT CTTCCCAAAC TCATGGAAAA     1740
ATGTATGATT GATTTGACGT AATATGGTAA TTGTTCCGTC ATCACATACA AAAACAGGTC     1800
CTATCAATGA AAGGTGGTAA ATGGATGAAA ATGTCATGTT TCCTCCCATT GATACATTAA     1860
AACATGGATT CCCCATCTAT AAAAACAGTG GCCCCAAACA AACGACAACA TACTCAACCG     1920
ACCACCGCAC TTTCAAGTTA AGTAACCATC CTTGGCAATT AAGAGTAAAA ATG GGA        1976
                                                         Met Gly
                                                         -22

CAA    G GTAAGCCTGC TTTTTCTGTC TATTTCTTTT TTCAGTGGGA AGTCAGAGTA       2030
Gln
-20

CCATTTAGTA CAATTTAACT ACTGCTATGA GGTTATAATC TATTGACACA GAACCACCTG     2090
CTTTAACAAC CTAACTATGT GATCCATAAC ATTTACATTT TTGTCATTTA GCAGACACTC     2150
TTTTCCAGAG CGACTTACAT GAGCAATTGG GGTTACGTGC CTTGCTCAAG GCACATCAG     2210
ATTTCTCACC TAGTCAGCTC TGGGGTTGAA ACCAGTAACC TTTCAGTTAC TGACCCAGCG     2270
CTCTTAACCA GCTAGGCTAT GGTGTACGA TGGCTGGGAA AATCTTACTA AGGTATCTCA      2330
CCATAATTCG ACTTACTCGT TTTCTACATT TGTTATTTGA ATCTCTCTTT TAG TG         2385
                                                           Val

TTT CTG CTG ATG CCA GTC TTA CTG GTC AGT TGT TTC CTG AGT CAA GGG      2433
Phe Leu Leu Met Pro Val Leu Leu Val Ser Cys Phe Leu Ser Gln Gly
-18         -15                 -10                     -5

GCA GCG ATA GAA AAC CAA CGG CTC TTC AAC ATC GCG GTC AGC CGG GTG      2481
Ala Ala Ile Glu Asn Gln Arg Leu Phe Asn Ile Ala Val Ser Arg Val
 1           5                    10
```

```
CAA CAT CTC CAC CTA TTG GCT CAG AAA ATG TTC AAT GAC TTT                     2523
Gln His Leu His Leu Leu Ala Gln Lys Met Phe Asn Asp Phe
 15                  20                  25

GTAAGACAGC TTTTGAATCT TCTTTGGACA TATCAAATAG TGTATCAATT ATTGTTCTTC            2583

TTCTTGTAGA CAGTGTCCTC TTCACACAAC CCTCGTGGCT AAAAGAATCT CTCTCTCCCT            2643

TTGTGATTTT GTGCAG GAC GGT ACC CTG TTG CCT GAT GAA CGC AGA CAG               2692
               Asp Gly Thr Leu Leu Pro Asp Glu Arg Arg Gln
                30                  35

CTG AAC AAG ATA TTC CTG CTG GAC TTC TGT AAC TCT GAC TCC ATC GTG             2740
Leu Asn Lys Ile Phe Leu Leu Asp Phe Cys Asn Ser Asp Ser Ile Val
 40                  45                  50                  55

AGC CCA GTC GAC AAG CAC GAG ACT CAG AAG AGT TCA GTAAGTAACC                  2786
Ser Pro Val Asp Lys His Glu Thr Gln Lys Ser Ser
             60                  65

TGGCTGAGAC AATTACGCAT GTTATGCCCT TTAGAACCAT ATAAAGTGTC AAATCGTGAC            2846

AGTTCCACTC TGCTATTCAC CTTAAATATG AACTCCTCCA TGATGCAAGA TTCCAAAAAT            2906

AAATAATAGG GCATCTCAAT TTGAACAATC GATAGAACTT AGTCATTAGT TATTGGGCAA            2966

GCAGACCACC AATTATGTAA ACTCAAATTT ATAATTTTTT ATTTAAATTT TATTTGAGCC            3026

TTTAATTAAC TTGGCAAGTC AGTTAAGAAC AAATTCTCAT TTACAATGAC AAGCAGAGGC            3086

AGCATCATGC ATGGCTCTCG AGTGGCACAG CAGTCTAAGG CACTACATCT CAGTGCCAGA            3146

GGTGTCACTG CAGACCCTAG TTCGATTCCA GACTGTATTT CAAACGGCTG TGATTGTGAG            3206

TCCATAGGGC GGCACACAAT TCTCCCAGCG TCGTTAGGGT TTGGCCGGGG TTGCAATACC            3266

TCAGTGTCTT CAACTAAGGT AGATAAAACA ACCACATATC ATTGCAAGTA AAACCATCAC            3326

TGTCTAATCG GTGGTTTCTC TATGTCTACA TTCTCTGTTT TGTGCTTTTC TGTACAGGAA            3386

ACCCACCCCA AAAGTATTTC ACTCAATCAT GTAAATAGGG CATCTCAAGC TGTAAATACA            3446

ACTCAACTTC ATTTTCCAAT AATCTGTGGT TTCTCTACAT CTTCACACAC AG GTC               3501
                                                           Val

CTG AAG CTG CTC CAT ATT TCT TTC CGT CTG ATT GAA TCC TGG GAG TAC             3549
Leu Lys Leu Leu His Ile Ser Phe Arg Leu Ile Glu Ser Trp Glu Tyr
 70                  75                  80

CCT AGC CAG ACC CTG ATC ATC TCC AAC AGC CTA ATG GTC AGA AAC GCC             3597
Pro Ser Gln Thr Leu Ile Ile Ser Asn Ser Leu Met Val Arg Asn Ala
 85                  90                  95                  100

AAC CAG ATC TCT GAG AAG CTC AGC GAC CTC AAA GTG GGC ATC AAC CTG             3645
Asn Gln Ile Ser Glu Lys Leu Ser Asp Leu Lys Val Gly Ile Asn Leu
                 105                 110                 115

CTC ATC ACG GTAAATAATG GAGAGAGAAC AATGACCATT TGTGGTCTCA                     3694
Leu Ile Thr

CACTTTGTGC ACTGTAAACT CCAAGGCATT TTTAACTCAA ATACTTCTAG TAAGTTGAAC            3754

TCAAGGTCAA TGAAAAATCC TTATTGCTTA AATGTTTAT GTGGTACTGG CTCAAAACTA            3814

AATGAGAAGT CACATCAATG CAATTTTTA AAGTTATAAC AAATTCACTT TTACCAAGCA            3874

TGCTCTACTG CAGGTAGATT TAAAAAAAAA AAAAAAAAA AAAAGAAGTT TTAATGATC             3934

TGTGTTTTTG CATGTACAGA ACATTGAGTG ATTGATTCAT TTATGCTAC ACAAAGATAT            3994

ATAACATACA TGTTTCAACG TTTTCATAAA GATGAACAAG TTACTAGAAT TTTGCAAACT           4054

CAACTTGCAG CCTGATGTGG CCTGTATACC GTGAGTTTCA GGCCACTGTA TTAGGGTAAA           4114

CTGACGCCTC AAAATAAGGT CTTATGAGAT AAGTAATGTA TTGTTGTAAA GAGTTGAATT           4174

CACTTGAAGG CCACAGGACT GAAAATGAAT GACAACAGCC ATGTCTCTGT CACTAACACA           4234
```

| | |
|---|---|
| TACAGTCATG GGTGATAACT ACACTTTACT CAAAAAGGCC AGGCACACTG GGAAATTATA | 4294 |
| TTTGAGACGT GGCTTAGTGG GGGCATTACT AAAAAATGTC AAGCTGATAC AACTCAAATC | 4354 |
| TGGACTCATC ACAGGGTGAA TCTATAGGTT TGAGTAATTA CTGACTATAA TATCACTTTA | 4414 |
| AGTAACTGCA GTCAGATTCT GTATATTAAG TGCAACGGTT TCCTAAAAAG TGTTGAGTAA | 4474 |
| TGGCAGCACA TTGGGGTTTA CAGTGACATG AAAGGGAAAT ACCTGTATGC TTTCCTAGTT | 4534 |
| AGAAAGCATA GTGTAAGGAC CACGTATGCC TCTTCTCAGC AGATCTTTCA GGGCTTTACA | 4594 |
| TTGTGATGTG GTAACTGACC TTATCTATCA TCGTGATTAT ATCAGTGACA CCCCATTCAA | 4654 |
| TGACTGAATA TCGCCCCATT CAAGGACATT TATCCATGTG TCTTTTGCTA CGTGTGCTTT | 4714 |
| CAGAAAGGCC CAATAAACAA ATATTGATAT GCACACATCC ACCCCACCAT GCATCTCTCT | 4774 |

```
CTGTCTCCAC AG GGG AGC CAG GAT GGC CTA CTG AGC CTG GAT GAC AAT            4822
              Gly Ser Gln Asp Gly Leu Leu Ser Leu Asp Asp Asn
              120             125             130

GAC TCT CAG CAA CTG CCC CCC TAC GGG AAC TAC TAC CAG AAC CTG GGG          4870
Asp Ser Gln Gln Leu Pro Pro Tyr Gly Asn Tyr Tyr Gln Asn Leu Gly
            135             140             145

GGC GAC GGA AAC GTC AGG AGG AAC TAC GAG TTG TTG GCT TGC TTC AAG          4918
Gly Asp Gly Asn Val Arg Arg Asn Tyr Glu Leu Leu Ala Cys Phe Lys
150             155             160

AAG GAC ATG CAC AAG GTGCCGAACC ATGTTGCCTT CAATTTATG TGCCTTCCTG           4973
Lys Asp Met His Lys
165
```

| | |
|---|---|
| TATTTTCTAC AGTGCGTTGT TTTTTTGTAT TCTCTATTGC AAAGTATTGT TAGTAAATAA | 5033 |
| CTCACGGACA CTAGAGAAGC TTTAACCAAG TTTAATTCTT CCCAAAGGTT CTGTACAGCT | 5093 |
| ATAATCAGAC AGCAAAACTT TCTCACTCCA CAGTCATATA TATCCTACTT AAAACACTCC | 5153 |
| TCCTTCTTCA ATCCTTACAG TTTATGGCTC CACAGGAAGC TAATAAAGCG GGTAACAGGA | 5213 |
| CAACAAACCT TTATTACTGC CTTCAGAGAA TCTGTCCTCA CCTCCTGACC TCGACCCCTC | 5273 |
| ATCTAATCCA CAGATGTATG TCCACCATTG TTTTTTTTTC AGAGAACCAT TAAGTTCTGA | 5333 |
| CATAACCCAG TTTCTTTCAT TTACTATCTC AATGATCAAC GTTAGCCGA TTCCAACAGT | 5393 |
| ATCTTTGGGT CTTTAACCCA TGTATTATTA CTATTATTGT TCATTGATCA AGACTGTTCT | 5453 |
| TGAGAAGTAT GGTGACCTAG AACACACACA TTAAAATGTG TCAACTATAA CCCATTCTTC | 5513 |

```
TTTTTTCCCC CCCGAG GTC GAG ACC TAC CTG ACC GTC GCC AAG TGC AGG           5562
              Val Glu Thr Tyr Leu Thr Val Ala Lys Cys Arg
              170             175

AAG TCA CTG GAG GCC AAC TGC ACT CTG TAGACGTGGG CTGGAGAGGC                5609
Lys Ser Leu Glu Ala Asn Cys Thr Leu
180             185
```

| | |
|---|---|
| TGCCAGCAAG AGCCTATCTC CAGGGTTCGG TTTCCCAGAT ACAGATTAGG CCTTGCCCTG | 5669 |
| CACTGAGGTG CATTTTCAAT TGAGATTCTC CATTAAACAT GCTTTTCAGT CTAGAGTAAT | 5729 |
| TTTATTTTGG ATCTGGTAGA GCCTGACTCC AGGGGTTTTC AGGCATTTGC ATTTTTTTCT | 5789 |
| CTGAAATCAA TAACAACACT TTCTATATTG ACTCTATCAC TCTGAGCTAC CATTGATTAG | 5849 |
| TACATTTATA TTAAAGGTTA TTAAATGTCT TATTTAGATA TATGGTTCAT GGCGGTGCTA | 5909 |
| CTTATGCATA CGTTAATATT TAGGGGTGAA ATGGGAACTT GTAGAGCTCC AAGCTTTGG | 5969 |
| ATAATATATT TTAGAGTAAT TTCCTTTAAG TATTTTCATT CCTTAATCTT ATTGTTTGAA | 6029 |
| ACTAATAGTG ATTCATGTTT CAATAAAGAT GTTCTTCTCT GCAGCACATG ATCTCTTGGC | 6089 |
| TTCTATTTAA TATCTTTCAA ATCAACATTT TTACAAGTT CCTAGCC | 6136 |

( 2 ) INFORMATION FOR SEQ ID NO:2:

( i ) SEQUENCE CHARACTERISTICS:
        ( A ) LENGTH: 5474 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinook Salmon ( i x ) FEATURE:
        ( A ) NAME/KEY: misc_feature
        ( B ) LOCATION: 1..5474
        ( D ) OTHER INFORMATION: /standard_name="Nucleotide
            Sequence of the Chinook Salmon GH Pseudogene"

( i x ) FEATURE:
        ( A ) NAME/KEY: exon
        ( B ) LOCATION: 1349..1414

( i x ) FEATURE:
        ( A ) NAME/KEY: intron
        ( B ) LOCATION: 1415..1810

( i x ) FEATURE:
        ( A ) NAME/KEY: exon
        ( B ) LOCATION: 1811..1950

( i x ) FEATURE:
        ( A ) NAME/KEY: intron
        ( B ) LOCATION: 1951..2086

( i x ) FEATURE:
        ( A ) NAME/KEY: exon
        ( B ) LOCATION: 2087..2203

( i x ) FEATURE:
        ( A ) NAME/KEY: intron
        ( B ) LOCATION: 2204..2660

( i x ) FEATURE:
        ( A ) NAME/KEY: exon
        ( B ) LOCATION: 2661..2816

( i x ) FEATURE:
        ( A ) NAME/KEY: intron
        ( B ) LOCATION: 2817..4769

( i x ) FEATURE:
        ( A ) NAME/KEY: exon
        ( B ) LOCATION: 4770..4853

( i x ) FEATURE:
        ( A ) NAME/KEY: intron
        ( B ) LOCATION: 4854..5003

( i x ) FEATURE:
        ( A ) NAME/KEY: exon
        ( B ) LOCATION: 5004..5474

( i x ) FEATURE:
        ( A ) NAME/KEY: misc_feature
        ( B ) LOCATION: 134..399
        ( D ) OTHER INFORMATION: /note="The 266 bp homologous
            region shared with GH-I in their 5'flanking
            regions."

( i x ) FEATURE:
        ( A ) NAME/KEY: misc_feature
        ( B ) LOCATION: 4836..4838
        ( D ) OTHER INFORMATION: /note="The premature stop codon in
            exon 5."

( x i ) SEQUENCE DESCRIPTION: SEQ ID NO:2:

```
AAGTCTAAAC  AACAACTGAA  CTTTTTGAGT  GATTTCTGAC  ATTTTGCTAC  AGGCAATACA        60
```

-continued

| | | | | | | |
|---|---|---|---|---|---|---|
|TATCCCACAA|TGGGGCCAGA|TATGAGATGT|TGGTTGATGG|AATAAAATAT|TTATTGATAC|120|
|ATGCTGTACA|TGAAGTATTT|TTGATTTGCT|GGACTATCAA|AACAAGTAAT|CACTACATCC|180|
|AGTCAAATAG|CCTGGCCAAA|ACTACCCATT|GTATAATGGT|CTTTTGAATG|CCAGCTATCA|240|
|CATATTCAAC|AAGGTCATGT|GGTCAGTAAA|TGCACTCGCT|GCCACCCTTC|CAAAGTGACG|300|
|CAGGTTAACA|GATCGATTTC|TGTTTTCGCC|AGGAAAGGAT|TAGGACAGTG|CTGGGCCTGA|360|
|CATTCAGCAC|GTCTCCATGT|CCTGAACGCT|GAATATGGAC|CTTGTTCACA|ACTAGCTGTT|420|
|GAATATGTGC|TCCCTGTATG|CCACAACGAC|AGACATCAAC|CATGAACTCA|TTACTCTCAA|480|
|TTGACCAGGT|AACCTTTATA|GTGGTCAAGA|CACAGTATAC|CTACACCTAC|CATTGTAGCA|540|
|TAAACTCAAC|ACAGTAAGGT|TGTGCGGCAC|AAACAGAGTG|AAGGCTTTGG|GCTAGTAGCG|600|
|CACATGCTGC|TTGGCTGCAA|GCATTCACGT|GTTATCCACT|GAGATGTGTA|CTTTTTTTAA|660|
|AGGCATATAG|ATTCTTACCC|CAAAATCAAT|CAATCAATCA|ATGAAGTATG|CCTACACAC|720|
|TTGCTCCAAC|AGATACCTTT|ATTGGTCTTC|GTCAGCTATA|ACACAGGCTC|TCACACAAAA|780|
|AGAAATGTG|GGTATTGATA|TAGTGACTGT|TTATGTTATT|TAAACAAACT|AAAAAACATA|840|
|CTTTGTAAGA|TGTGTGTCTC|CAGATAGTTC|CTTCTCTGTG|TGTCTACTTT|GAGGTCTGTG|900|
|CTAACACCAT|AGGACATTCA|ATTGACATTA|AACAATAAAA|TATTGGTGCT|AATAAAGAAG|960|
|CAATATAATA|TATTTGTCAA|ATAATGCCTG|TTATTTACAG|TACCGCGGAA|CGGCAGAATA|1020|
|ACCGGTGTTG|TTGTCAAGTT|ACATGTCTGT|CTGTGTGTGA|GTGTAACTTT|TGTTCATTCA|1080|
|TTATGTCCTA|GACAACAGAG|GTTTGTTTTG|TATGTGTTTT|GACCCTAATT|TGTCAAGTAA|1140|
|GTTTTTTTGT|AGGAGAGTCA|CCAGTTCCTG|AACTCATGGA|AAAATTCATG|ATTGATTTGA|1200|
|CGTATTATAC|TGATTGTTCC|ATAATGGCAT|ACAAAAACAG|GTTACATCAG|CGACAGGTGG|1260|
|TAAATGGCGA|AAATCTCATG|TTTACTCATG|TTGATACATT|AAAACATATG|TTCCCCATCT|1320|
|ATAAAAACAG|TGGCCGCAAA|CGAAGGGCTA|ACCACATCAG|CCACCACACT|GTCAAGTCAT|1380|
|CATCCTTGGC|AATTAAGAGA|AGAAATCTGA|CTTGGTAAAC|CAGCTTTTAT|TTTCCTTTTT|1440|
|TAAGTGAGAA|GTCAGTGTAC|CATTTAATAC|CATTTAACTT|TAACATTTAA|ACATTTAACA|1500|
|TTAACATTAC|TAGTTACAAC|CTAACTATGT|GATCTATTAG|ATTTACATTT|TAGTTATTTA|1560|
|GCAGACAGTC|TTATCCAGAG|TGACTTACAG|GAGCAATTAG|GGTTAAGTGC|CTTGCTCAAG|1620|
|GGCACATCAA|CAGATTTCTC|ACCTAGTCAA|CTCAGGGATT|CAAACCAGTA|ACCTTTCAGT|1680|
|TACTGGCCCA|ACGCTCTTAA|TCGCTAGGCT|ATTGATGTAC|CAAGGCTGAG|AATATCTTAC|1740|
|TAACATGTCG|CAACATAATT|TGACTTACTT|GTTTTATAC|ATTGCTTATT|TTCTTTCATC|1800|
|TGACTTTTAC|TGTTTCTGCT|GATGCCAGTC|TTACTGTTCA|GTTGTTTTCT|GGGTCAAGGG|1860|
|GAAGTGATGG|AAAACCAACA|GCTCTTCAAC|ATTGCAGTCA|ACAGGGTGCA|ACAGTTCCAC|1920|
|CTATTGGCTC|AGAAAATGTC|CAACGACTTT|GTAAGACATA|TTTTGAATCT|TCTTTTGACA|1980|
|TAGCAGATCA|TGTTTCAGAG|GTGATTCTTC|TTCTTGTAAA|CAGTGTCCTC|TTCACACAAA|2040|
|CCTAGCGGCA|AAAAATTCTC|TCTCCCTTCT|GTGTGATTTT|GTGCAGGAAG|GCACCCTGTT|2100|
|TTCTGATGAA|CGCAGACAGC|TGAACAAGAT|ATCCCAGCTG|GACATCTATA|ACTCTGACTT|2160|
|CATCATGAGC|CCAATCGACA|AGCAGGAGAC|TCAGAAGACT|TCAGTAAGTT|ACCTGGCGGA|2220|
|GCAAATCCGC|ACGATGCACG|ATTCCAAAAT|TAATAATAGG|GCATCTCAAT|TTGAATAATC|2280|
|GATACAACTT|AGTCATTAGT|TATTGGGCAA|GCAGATCCCC|GATTGGTCTA|AACTCCATGG|2340|
|GTAAATATAT|ACTGTAGGAA|AGCAGAACCA|GCATCATGCA|TGGTGGAAAT|TAAATCTAGC|2400|

-continued

```
CATGATAGGG AGTTTTAAAT TGTACACTTA AAATCAGCCA GTAAATGTT  GCTATACCTC  2460
AGTGCCTTCA ATTAAGGTAG TTAAAACAAC CACACACCAT AGTCCTTGTA AGTAAAACTC  2520
ATCACTCTCT AATCGGCGGT TTCTCTACAT CTACATTCTC CAGCCATGTA TCATGTAAAT  2580
GATATGTCAT CTCAAGCTGT ACAATACAAT TCAACTTCAT TTTCTAATAA TCTGTGGTTT  2640
CTCTACATCT ACACACACAG GTCCTTAATC TTCTCCATAT CTCTTTCCAC CTGATTGAAT  2700
CCTGGCAGTA CTCTAGCCAG ACCATGACCA TCTCAAACAG CCTGATGGTC AGAAACTCCA  2760
ACCAGATCTC GAAGAAGCTC AGTGACCACA AAGTGGGCAT CAACCTGCTC ATCAAGGTAA  2820
AGAAAGGAGG GAGAACAATG ACCATTGTGG TGCCGACTTT GTGCATTTAT AACTCAAATA  2880
CTTCTAGTAA GTTGAACTCA GTCAAGTCAT TATTAAAATG TCTATGTGCT ACTGGCTCAC  2940
ATCTAAATGA GTCACATCAA TGCAAGTTTT TAAAGTTATA ACAAATTAAC TTTTTACCCA  3000
GCATGCTCTA CTACAGGTAG ATTGTTTTTG GAATTGTTCT TAATATCTGT GTTTTACAT   3060
GTACAGTACA TTGCTGGCTG CCGCTCCAGC CCACGTTTAC ACTACATTGA GTGATTGATT  3120
AGATTATTAA TCTTATGCTA CGGAATCTAA AATAAAAATC CCGAAAATCA TATTGTATCA  3180
TTTTTAAGTC ATTCATTTGC AGTTCATTGC ATGACATAAG AATTTGATCA CCTACCAACC  3240
AGTAAGAATT ACGGCTCTTA CAGACCTATA TTTTTATATT GTCTTTGCAA TGGGATATTT  3300
CATAGGAACC AATTTTTTTC CCCTACCGCT TCCGCTGGAT GTTGCCAGTC TTTGGAATTT  3360
GGTTGAGGTT ATTTCTTTGT GCCATGAAGA AGTAGGACAA CTCGGAACTG GGACACTTT   3420
TGTGAGTTGA GCAAGATGTG AAATCCAGTG CTGGTTTCTT TTCTTTCCTG TACAGATTGC  3480
CGTCTACAAT TTGATTGATT ATTAACATTT AAAAATACCC AACGTTGTAT TACAAAAGTA  3540
GTTTGAAATA TTTTGGCAAA TTTTATAAGA CAACTTTTGA AATATTTGT AGCGATGTTG   3600
CGTTTTTGTA AGCTGTCTTT TTCTGGATCA AACGCTCTTT ATAAAGGGAC ATTTTCAATA  3660
TATATGGACG GAATTAATCA AACAAAGGA  CCAATTGTGA TGTTTATGGG ACATATTGGA  3720
GTGCCAACAA AAGAAGCTCG TCGAAGGTAA TGCATGTTTT TTATATTTTT ATTTCAGCGT  3780
TTTTGTGTAG CGCCTGCAGG GTTGTAATAT GCTAGCTCCT TTGTTTACTG CTGGTGCAGA  3840
TGGTACAGGC TATCAGATAA TAGCTTCTTA CTGTTTCGCC GAAAAGCAGT GTAAAATCT   3900
GACATGTTAG CTGGATTCAC AACGAGTGTA TAGCTTTAAT TGAGTATCTT ACATGTGTGA  3960
TTTAATGAAA GTTTGAATCT TATAGCATTT ATTTGAATCT GGGTGCTCTG CATTTCCCCC  4020
CAGCAATTGG CCAGTTGAGA CGTTAGCATC TCGGCTATCT GTAAGAGTTA AGAATCCCTC  4080
CTGTTCTCCA CTCATACCTG TATTAACTGC ACCTGTTTGA ACTCATTACC TGTATACAAG  4140
ACACCTGTCC ACACACACAA TCAAACAGAC TCCAACCTCT CCACAATGGC CAAGACCAGA  4200
GGGCTGTGTA AGGGCATCAG GGTTACAAAT GTAGACCTGC ACAAGGCTGG GATGGGCTAC  4260
AGGAAAATAG GCAAGCAGCT TGGTGAGAAG GCAACAACTG TTGGCGCAAT TATTAGAAAA  4320
TGGAAGAAGT TCAAGATGAC GGTCAATCAC CCTTGGTCTG GGCTCCATG  CAAGATCTCA  4380
CCTCGTGGGG TATAAATGAT CATGAGGAAG GTGAGGGATC AGCCCAGTGT AGCTGCAGGA  4440
CCTGGTCAAT GACCCGAAGA GAGCTGGGAG CACAGTCTCA AAGAAAACCA TTAGTAACAC  4500
ACTACGCCGT CATGGATTAA AATCCTGCAG TGCATGCAAG GTCCCCTGC  TCAAGCCAGC  4560
GCATGTCCAG GCCCGTCTGA AGTTTTCCAA TTACCATCTG GATGATCCGG AGGGGAATGG  4620
GAGAAGGTCA TGTGGTCTGA TGAAACAAAA ATAGAGCTTT TTTGTCTAAA CTCCACTCGC  4680
TGTGTTTGGA GGAAGAAGAA GTATGAGTCG GGGATTTGTA TTGATATGCA AACATCCACC  4740
CCACCATGCA TCTCTCTCTG TCTCCACAGG GGAGCAAGGA TGGGATACTG ATCCTGGGTG  4800
```

```
ACAATGACTC  TCAGCATCTG  CCCCCCTGCG  GGAACTAATA  CCAGAACCTG  GGGCGAACCT      4860

GGACGTATCT  TTGGGTCTTT  AATCCATATA  TGATTTCTAT  TATTGTTCAT  TGATCAAGAC      4920

TGGTCTCGAG  AAAGTCCTAG  TGACATAGAA  CATTCACATT  AAAATGTGTC  AAATATAACC      4980

TATTCTTCTT  TTTTCCCCCC  AAGGTTGAGA  CCTACCTGAC  CGTCGCTAAG  TGCAGGCAGT      5040

CGCTGGAGGC  CAACTGCACT  CTGTAAACGT  GGGCTGGAGC  GGCAGCCAGC  AAGAGCTGTC      5100

TCCAGGGTTC  GGTTTCCCAG  ATACAGATTA  CACCTTGCTC  TGCACTGAAG  AGCATTTTCA      5160

ATTGAGATTC  TCCATTATGC  ATGCTTTTA   GTCTATAGTA  GATTAATTAG  TAGATTTAAT      5220

TTAGATCTGG  TAGAGCCTGA  CTCCAGGGGT  TTTCAAGCAT  TTGCATTTTC  TTCTCTGAAA      5280

TCAACAACAG  CACTTTCTAT  AATATTCACT  CTATTCCTCA  GAGCTACCAT  TGATCCACGG      5340

ACATTTTAGA  TTAGTACATT  TATAGAAAAG  ATTATAAATA  TGTCTTATTT  AAATATATGA      5400

TTCGAGGTGG  TGCTGCCATT  TATGCATAAA  TTAATATTTA  GGGGTGAAAT  GGGAACTTGT      5460

AGAGCTCCAA  GCTT                                                            5474
```

( 2 ) INFORMATION FOR SEQ ID NO:3:

( i ) SEQUENCE CHARACTERISTICS:
        ( A ) LENGTH: 401 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinook Salmon ( i x ) FEATURE:
        ( A ) NAME/KEY: misc_feature
        ( B ) LOCATION: 1..401
        ( D ) OTHER INFORMATION: /standard_name="Partial DNA
            Sequence of Chinook Salmon GH-II Gene"
        / note="Sequence spans from the 3'end of exon 5,
        intron 5 and 5'end of exon 6."

( i x ) FEATURE:
        ( A ) NAME/KEY: misc_feature
        ( B ) LOCATION: 1..124
        ( D ) OTHER INFORMATION: /standard_name="3'end of exon 5"

( i x ) FEATURE:
        ( A ) NAME/KEY: misc_feature
        ( B ) LOCATION: 125..339
        ( D ) OTHER INFORMATION: /standard_name="Intron 5"

( i x ) FEATURE:
        ( A ) NAME/KEY: misc_feature
        ( B ) LOCATION: 340..401
        ( D ) OTHER INFORMATION: /standard_name="5'end of exon 6"

( x i ) SEQUENCE DESCRIPTION: SEQ ID NO:3:

```
CCTGGATGAC  AATGACTCTC  AGCATCTGCC  CCCTACGGG   AACTACTACC  AGAACCTGGG       60

GGGCGACGGC  AACGTTAGGA  GGAACTACGA  ACTGTTGGCC  TGCTTCAAGA  AGGACATGCA      120

TAAGGTGGAA  GATCACGTTG  CCTTCAATTG  CATGTGCCTT  CCTATATTTT  CTACGGTGCA      180

TTGTTTTTTT  TGTAATCTCT  ATTGTGAAGC  CTTTGGGTCT  TCAACCCATA  TGTTATTACT      240

ATTATTGTTT  ATTGATCAAG  ACTGGTCTCG  AGAAAGTCCT  GGTGACTTAG  AACATGCACA      300

TTAAAATGTG  TCACTATAAC  CTATTCTTCT  TGTCCCAAGG  TTGAGACCTA  CCTGACCGTC      360

GCTAAGTGCA  GGAAGTCACT  GGAGGCCAAC  TGCACTCTGT  A                          401
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinook Salmon ( x i ) SEQUENCE DESCRIPTION: SEQ ID NO:4:

CCTGGATGAC AATGACTCTC A        21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinook Salmon ( x i ) SEQUENCE DESCRIPTION: SEQ ID NO:5:

CTACAGAGTG CAGTTGGCCT C        21

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinook Salmon ( x i ) SEQUENCE DESCRIPTION: SEQ ID NO:6:

GAAAATGTTC AATGACT        17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinook Salmon ( x i ) SEQUENCE DESCRIPTION: SEQ ID NO:7:

CTCTATCACT CTGAGCT        17